United States Patent
Wang et al.

(10) Patent No.: US 10,067,111 B2
(45) Date of Patent: Sep. 4, 2018

(54) SYSTEM AND METHOD TO MEASURE DISSOLVED GASES IN LIQUID

(71) Applicant: Woods Hole Oceanographic Institution, Woods Hole, MA (US)

(72) Inventors: Zhaohui 'Aleck' Wang, N. Falmouth, MA (US); Frederick N. Sonnichsen, E. Falmouth, MA (US)

(*) Notice: Subject to any disclaimer, the term of this patent is extended or adjusted under 35 U.S.C. 154(b) by 287 days.

(21) Appl. No.: 14/722,370

(22) Filed: May 27, 2015

(65) Prior Publication Data
US 2015/0346178 A1    Dec. 3, 2015

Related U.S. Application Data

(60) Provisional application No. 62/003,233, filed on May 27, 2014.

(51) Int. Cl.
G01N 21/31 (2006.01)
G01N 21/78 (2006.01)
(Continued)

(52) U.S. Cl.
CPC ......... G01N 33/1886 (2013.01); G01N 15/06 (2013.01); G01N 21/05 (2013.01); G01N 21/31 (2013.01); G01N 21/78 (2013.01); G01N 31/221 (2013.01); G01N 33/1893 (2013.01); G01N 2015/0011 (2013.01);
(Continued)

(58) Field of Classification Search
CPC ........... G01N 15/06; G01N 2015/0011; G01N 2015/0687; G01N 2015/0693; G01N 21/05; G01N 21/31; G01N 21/78; G01N 31/221; G01N 31/1886; G01N 33/18; G01N 33/1846; G01N 33/1886; G01N 33/1893; Y10T 436/117497; Y10T 436/175383;
(Continued)

(56) References Cited

U.S. PATENT DOCUMENTS

| | | | |
|---|---|---|---|
| 7,087,436 B2 * | 8/2006 | Baumgardner | H01J 49/0436 250/281 |
| 9,772,293 B2 * | 9/2017 | Nakano | G01N 21/78 |
| 2015/0246314 A1 * | 9/2015 | Constantz | B01D 53/62 423/220 |

FOREIGN PATENT DOCUMENTS

WO    2014/104128    * 7/2014

OTHER PUBLICATIONS

Liu et al. Environmental Science and Technology, vol. 47, Aug. 30, 2013, pp. 11106-11114.*

(Continued)

*Primary Examiner* — Maureen Wallenhorst
(74) *Attorney, Agent, or Firm* — Douglas Denninger

(57) ABSTRACT

A high-resolution in situ sensing system and method for providing continuous measurements of at least one dissolved gas including a sample liquid processing cell having at least a first conduit defining a first passage with at least one gas-permeable wall capable of passing the at least one pre-selected dissolved gas from the sample liquid into a reagent fluid. The at least one gas-permeable wall substantially resists flow of the sample liquid therethrough. Reagent fluid is directed through the first conduit while moving the sample liquid and the reagent fluid relative to each other in one of a concurrent and a countercurrent flow relationship to achieve either partial or full equilibration between the sample liquid and reagent fluid to generate at least partially equilibrated reagent fluid in a substantially continuous manner.

26 Claims, 18 Drawing Sheets

(51) Int. Cl.
  *G01N 31/22*   (2006.01)
  *G01N 33/18*   (2006.01)
  *G01N 35/08*   (2006.01)
  *G01N 15/06*   (2006.01)
  *G01N 21/05*   (2006.01)
  *G01N 15/00*   (2006.01)

(52) U.S. Cl.
  CPC .............. *G01N 2015/0687* (2013.01); *G01N 2015/0693* (2013.01); *Y10T 436/117497* (2015.01); *Y10T 436/204998* (2015.01); *Y10T 436/235* (2015.01); *Y10T 436/255* (2015.01)

(58) Field of Classification Search
  CPC ....... Y10T 436/204998; Y10T 436/235; Y10T 436/255; Y10T 436/2575
  USPC ... 436/52, 68, 113, 133, 145, 146, 163, 164, 436/165, 167, 168, 178, 180; 422/81, 422/82.05, 82.09, 535
  See application file for complete search history.

(56) References Cited

OTHER PUBLICATIONS

Wang et al. Environmental Science and Technology, vol. 49, Feb. 26, 2015, pp. 4441-4449.*
Wang et al. Analytica Chimica Acta, vol. 596, 2007, pp. 23-36.*
Egleston, E. S. et al., Revelle revisited: Buffer factors that quantify the response of ocean chemistry to changes in DIC and alkalinity. Global Biogeochem. Cycles, 2010, pp. 1-9, vol. 24. GB1002, doi:10.1029/2008GB003407, Amer. Geophys. Union.
Fabry, V.J. et al., Impacts of ocean acidification on marine fauna and ecosystem processes. 2008, pp. 414-432, V. 65 (3) J. Mar. Sci., ICES.
Feely, R.A. et al.,Ocean Acidification: Present Conditions and Future Changes in a High-CO2 World. 2009, pp. 36-47, V. 22(4), Oceanography.
Le Quere, C. et al., Impact of climate change and variability on the global oceanic sink of CO2, 2010, pp. 1-10, V. 24, Global Biogeochem. Cy. DOI: 10.1029/2009GB003599.
Li, Q.L. et al.,Automated spectrophotometric analyzer for rapid single-point titration of seawater total alkalinity. 2013,pp. 11139-11146, V. 47 (19),Environ. Sci. Technol.
Liu, X.W. et al., Purification and characterization of meta-cresol purple for spectrophotometric seawater pH measurements, 2011, pp. 4862-4868, vol. 45 (11), Environ. Sci. Technol., Amer. Chem. Soc.
Liu,X.W. et al., Spectrophotometric measurements of pH in-situ: Laboratory and field evaluations of instrumental performance, 2006, pp. 5036-5044, vol. 40(16), Environ. Sci. Technol., Amer. Chem. Soc.
Martz, T.R. et al., Testing the Honeywell Durafet (R) for seawater pH applications, 2010, pp. 172-174, V.8, Limnol Oceanogr-Meth., Amer. Soc. Limn. Oceanogr.
Nakano, Y. et al.,Simultaneous vertical measurements of in situ pH and CO2 in the sea using spectrophotometric profilers, 2006, pp. 71-81, V.62(1), J. Oceanogr.
Orr, J.C. et al.,Anthropogenic ocean acidification over the twenty-first century and its impact on calcifying organisms, 2005, pp. 681-686, V. 437, Nature, Nature Publ. Group, Doi 10.1038/Nature04095.
Seidel, M.P. et al., A sensor for in situ indicator-based measurements of seawater pH,2008,pp. 18-28, V.109 (1-2), Mar. Chem. DOI 10.1016/j.marchem.2007.11.013.
Wang, Z.A. et al.,High-frequency spectrophotometric measurements of total dissolved inorganic carbon in seawater, 2013, pp. 7840-7847, V.47, Environ. Sci. Technol.
Wanninkhof, R. et al.,Global ocean carbon uptake: magnitude, variability and trends, 2013, pp. 1983-2000, V.10, Biogeosciences, Eur. Geos. U.
Yao, W.S. et al., Spectrophotometric determination of freshwater pH using bromocresol purple and phenol red, 2001, pp. 1197-1201, V.35(6), Environ. Sci. Technol., Amer. Chem. Soc.
Zhang, H.N. et al., Spectrophotometric pH measurements of surface seawater at in-situ conditions: Absorbance and protonation behavior of thymol blue, 1996, pp. 17-25, vol. 52, Mar. Chem., Elsevier Sci. B.V.

* cited by examiner

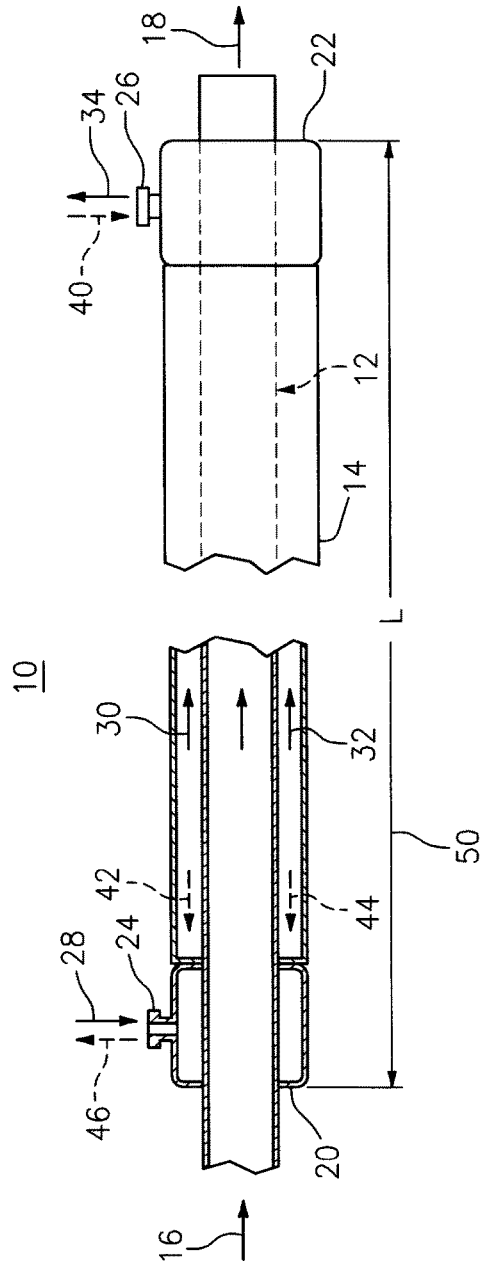
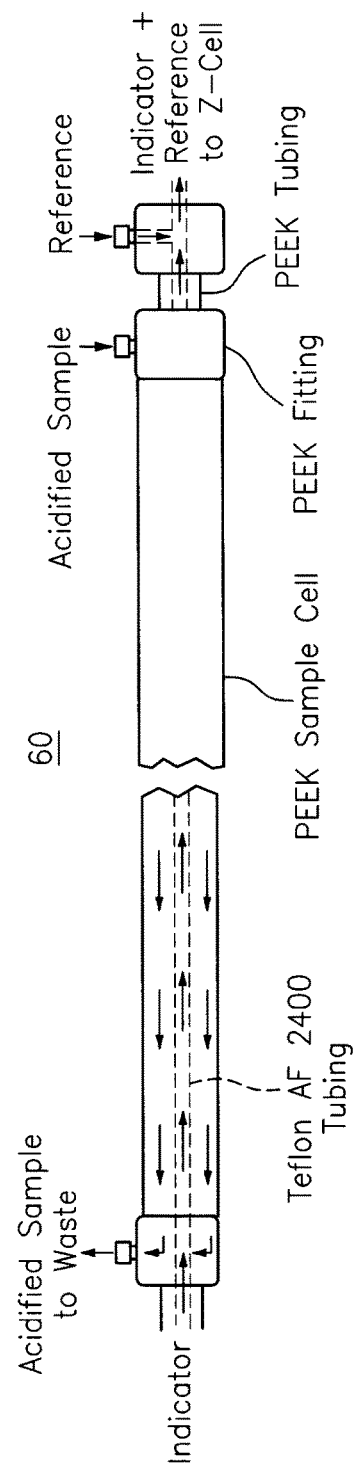
FIG. 1A
FIG. 1B

SYSTEM AND METHOD TO MEASURE DISSOLVED GASES IN LIQUID

CROSS-REFERENCE TO RELATED APPLICATION

This application claims priority to U.S. Provisional Application No. 62/003,233 filed 27 May 2014. The entire contents of the above-mentioned application is incorporated herein by reference.

STATEMENT REGARDING FEDERALLY SPONSORED RESEARCH

Federal funds awarded by the U.S. National Institute of Standards and Technology under Grant No. 60NANB10D024 and the U.S. National Science Foundation under Grant Nos. OCE-1041068 and OCE-1233654 contributed to making the invention. The U.S. Government has certain rights herein.

FIELD OF THE INVENTION

The invention relates to systems and methods of measuring dissolved gases and more particularly to dynamic, real-time measurements within a liquid such as seawater.

CROSS-REFERENCE TO RELATED PUBLICATIONS

This application incorporates the entire contents of the following publications by reference: Wang et al., High-Frequency Spectrophotometric Measurements of Total Dissolved Inorganic Carbon in Seawater. Environ. Sci. Technol. 2013, 47: 7840-7847, and Wang et al., In Situ Sensor Technology for Simultaneous Spectrophotometric Measurement of Seawater Total Dissolved Inorganic Carbon and pH. Environ. Sci. Technol. 2015, 49: 4441-4449. The entire contents of the above-mentioned publications are incorporated herein by reference in their entirety.

BACKGROUND OF THE INVENTION

The marine carbon dioxide ($CO_2$) system plays a critical role in regulating $CO_2$ fluxes into and out of the world's oceans. One of the primary mechanisms by which the ocean affects the Earth's climate is through regulating $CO_2$ gas into and out of the ocean via the marine $CO_2$ system. Currently, the ocean absorbs about one third of the anthropogenic $CO_2$ released to the atmosphere by human activities, thus playing a major role in reducing the rate of atmospheric $CO_2$ increase and thereby curbing global warming. However, oceanic uptake of anthropogenic carbon is causing a rapid change in seawater carbonate chemistry, often referred to as ocean acidification, wherein excess $CO_2$ lowers seawater pH, increases total $CO_2$ concentration, and decreases calcium carbonate saturation. Changes in the marine $CO_2$ system may result in complicated responses and feedbacks in the ocean, ranging from changes in marine carbon and other elemental cycles to marine biology and ecology. Ocean acidification also reduces seawater buffering capacity, slowing down oceanic carbon uptake and acting as a positive feedback to the atmospheric $CO_2$ increase The four primary parameters used to characterize the marine $CO_2$ system are total dissolved inorganic carbon (DIC), partial pressure of $CO_2$ ($pCO_2$) or $CO_2$ fugacity ($fCO_2$), pH, and total alkalinity (TA). DIC is defined as the sum of all carbonic acid species in water: $DIC = CO_2^* + HCO_3^- + CO_3^{2-}$, where $CO_2^*$ is the sum of dissolved $CO_2$ and carbonic acid ($H_2CO_3$). DIC is a master carbon parameter frequently used to study, identify, and differentiate many processes linked to the marine carbon cycle (e.g. biological uptake of $CO_2$, ocean acidification, and anthropogenic $CO_2$ penetration in the ocean). The assessment of these processes ultimately relies on high-quality measurements of seawater DIC. In addition, to fully characterize the $CO_2$ system through thermodynamic calculations, at least two $CO_2$ parameters must be measured. $CO_2$ calculations made using DIC data as one of the parameters yield results that are often more consistent with measured values. Because of its important role in the $CO_2$ system, DIC was measured during all of the major ocean carbon expeditions, such as the Climate Variability and Predictability (CLIVAR) Hydrography Program and the Joint Global Ocean Flux Study (JGOFS).

Theoretically, measurements of any two of the four parameters along with salinity and temperature can be used to calculate the other parameters and fully resolve carbonate chemistry using seawater acid-base equilibria. However, selection of different measurement pairs in practice will generate a range of calculation errors resulting from analytical errors, uncertainties in equilibrium constants, and their non-linear propagation in calculation. Using DIC or TA as one of the measured pair produces relatively small calculation errors, while selection of the $pCO_2$-pH pair for measurements causes large calculation bias even under the best analytical practice. Only in situ $pCO_2$ and pH measurements have become increasingly common in recent years on various platforms, such as buoys and profilers, as commercial $pCO_2$ and pH sensors are available. In contrast, in situ sensing for DIC and TA are much less mature, and are mostly under different development stages. Simultaneous, in situ measurements of two $CO_2$ system parameters with either DIC or TA as one of the two are highly desirable but extremely rare.

Traditional bottle sampling and subsequent analysis of DIC can only achieve limited spatiotemporal coverage mainly because of associated high costs and low throughput. Development of methodologies that are suitable for high-resolution in situ measurements of $CO_2$ parameters have been widely recognized as a research priority in the carbon and ocean acidification research community. Among various methods (e.g. coulometry, potentiometry, non-dispersive infrared (NDIR) method, and conductimetry) developed for high-precision DIC measurements, the spectrophotometric method offers high sensitivity, good stability, and direct measurements of water-phase samples. It can be 'calibration-free' in theory, thus reducing maintenance requirements. These attributes make it well suited for in situ underwater applications.

The existing spectrophotometric DIC method is based on spectrophotometric pH measurements where observed absorbances of a sulfonephthalein indicator liquid and its equilibrium properties are used to quantify sample pH. A piece of Teflon AF 2400 (DuPont™ copolymer) capillary tubing is used as both an optical cell and a $CO_2$ equilibrator as it is highly permeable to $CO_2$ molecules and can act as a liquid-core waveguide (LCW) for optical detection. The spectrophotometric detection occurs after full $CO_2$ equilibration is established between the acidified sample and the indicator solution across the Teflon AF tubing. The indicator solution is motionless during the equilibration process. This method is similar in principle to the spectrophotometric $fCO_2$ method, but the sample is not acidified and a different indicator is used. Because the indicator does not directly mix with the sample in either of these methods, no dilution or perturbation to the seawater sample occurs.

The response time (i.e. the time required to obtain a stable reading for detection) of the existing spectrophotometric method is about 5 minutes, which is the $CO_2$ exchange time required to reach full $CO_2$ equilibration. This method has been used for underway measurements of flow-through seawater, and actual measurements are intermittent. Such a response is sufficient for some stationary measurements, such as bottle samples and buoy deployments, where discontinuous measurements are acceptable. However, it is not ideal for high-resolution measurements made on mobile platforms, particularly those such as Automated Underwater Vehicles (AUVs), Remotely Operated Vehicles (ROVs), gliders, or water-column profilers. At the 5-minute sampling interval, the spatiotemporal resolution on these mobile platforms may be limited for studying rapid changes on a scale down to minutes or meters and fine-scale features such as those encountered in coastal oceans and water-column profiling.

SUMMARY OF THE INVENTION

This invention features systems and methods that rapidly and at least substantially continuously measure at least one pre-selected dissolved gas, such as dissolved carbon dioxide, within a sample liquid such as freshwater or seawater obtained from a quantity of the liquid such as a pond, lake, stream, bay, or ocean. The system and method include selecting a sample processing cell having at least a first conduit defining a first passage with at least one gas-permeable wall capable of passing at least the pre-selected dissolved gas from the sample liquid into a reagent fluid. The at least one gas-permeable wall substantially resists flow of the sample liquid therethrough, that is, it maintains liquid separation between the sample and reagent fluids. The system and method further include directing reagent fluid through the first conduit while moving the sample liquid and the reagent fluid relative to each other in one of a concurrent and a countercurrent flow relationship to achieve either partial or full equilibration between the sample liquid and reagent fluid to generate at least partially equilibrated reagent fluid in a substantially continuous manner. The quantity of the dissolved gas in the at least partially equilibrated reagent is measured by spectrophotometry (using an indicator solution as the reagent) or other measurement techniques. The sample liquid is obtained at least substantially continuously from the quantity of the liquid, preferably while the sample processing cell is immersed in the quantity of liquid. Measurement systems according to the present invention are suitable for installation and use in situ on Autonomous Underwater Vehicles (AUVs), Remotely Operated Vehicles (ROVs), gliders, profilers, and other mobile or stationary platforms, preferably to perform sampling and measurements at depths of at least 3,000 m or greater.

The term "reagent" as utilized herein refers to an indicator fluid or solution, preferably a liquid for submersible applications, for conducting spectrophotometric sensor measurements and refers to other types of fluids for conducting other types of sensor measurements. In some constructions, the indicator solution is a pH indicator employed to produce a colorimetric change or other detectable chemical reaction in the presence of shift in other signals.

This invention also features an in situ sensing system, referred to herein as Channelized Optical System (CHANOS) or Dual-channel Modularized Autonomous System (D-MAS), that is capable of making high-resolution, simultaneous measurements of at least two parameters such as total dissolved inorganic carbon (DIC) and pH in seawater. Measurements made by this single, compact sensor can fully characterize the marine carbonate system. The system preferably has a modular design to accommodate two independent, but similar measurement channels for DIC and pH. Both are based on spectrophotometric detection of hydrogen ion concentrations. The pH channel preferably uses a flow-through, sample-indicator mixing design to achieve near instantaneous measurements. The DIC channel utilizes the spectrophotometric method described herein to achieve flow-through $CO_2$ equilibration between an acidified sample and an indicator solution with a response time of only ~90 s. During laboratory and in situ testing, CHANOS achieved a precision of ±0.0010 and ±2.5 µmol kg$^{-1}$ for pH and DIC, respectively. In-situ comparison tests indicated that the accuracies of the pH and DIC channels over a three-week time-series deployment were ±0.0024 and ±4.1 mmol kg$^{-1}$, respectively. CHANOS can make in-situ, climatology-quality measurements by measuring two desirable $CO_2$ parameters, and is capable of resolving the $CO_2$ system in dynamic marine environments.

The CHANOS sensor is among the first that is able to fully resolve carbonate chemistry with a single system and a desirable pair of $CO_2$ system parameters measured to achieve small calculation errors. The CHANOS preferably has a build-in mechanism for in situ calibration, which ensures high measurement quality throughout a deployment and reduces the need for laboratory calibration. Preferably, the system is able to make high-resolution, climatology-quality measurements to resolve seawater-$CO_2$ system dynamics.

This invention further features a new spectrophotometric DIC method capable of attaining a much faster response time (approximately 70 seconds for full equilibrium and approximately 22 seconds for 60%-70% partial equilibrium in one embodiment wherein indicator fluid has a transit time of approximately 10 seconds) using flow-through (dynamic) $CO_2$ equilibration by introducing countercurrent, continuous flow between the indicator solution and the sample, as described below for FIGS. 1B and 2A. This embodiment allows for continuous measurements as compared to intermittent measurements made with the existing intermittent spectrophotometric method. The present method has achieved good measurement stability and repeatability, similar to those of the intermittent method. During field tests, the continuous method of the present invention produced high-resolution DIC data that were in good agreement with measurements made by the established Non-dispersive Infrared (NDIR)-based method. These characteristics make the continuous method particularly suitable for expanding observational capabilities of the $CO_2$ system on mobile observing platforms.

BRIEF DESCRIPTION OF THE DRAWINGS

In what follows, preferred embodiments of the invention are explained in more detail with reference to the drawings, in which:

FIG. 1A is a schematic, partial cross-sectional view of a sample processing cell utilized according to the present invention for either concurrent or countercurrent flow of sample fluid relative to a reagent fluid;

FIG. 1B is a schematic, partial cross-sectional view of a sample processing cell utilized according to the present invention for countercurrent flow utilizing Teflon AF tubing;

FIG. 10B shows all experimental DIC data with a higher R Ratio scale on the y-axis;

DETAILED DESCRIPTION OF PRESENTLY PREFERRED EMBODIMENTS

Figure 2A:
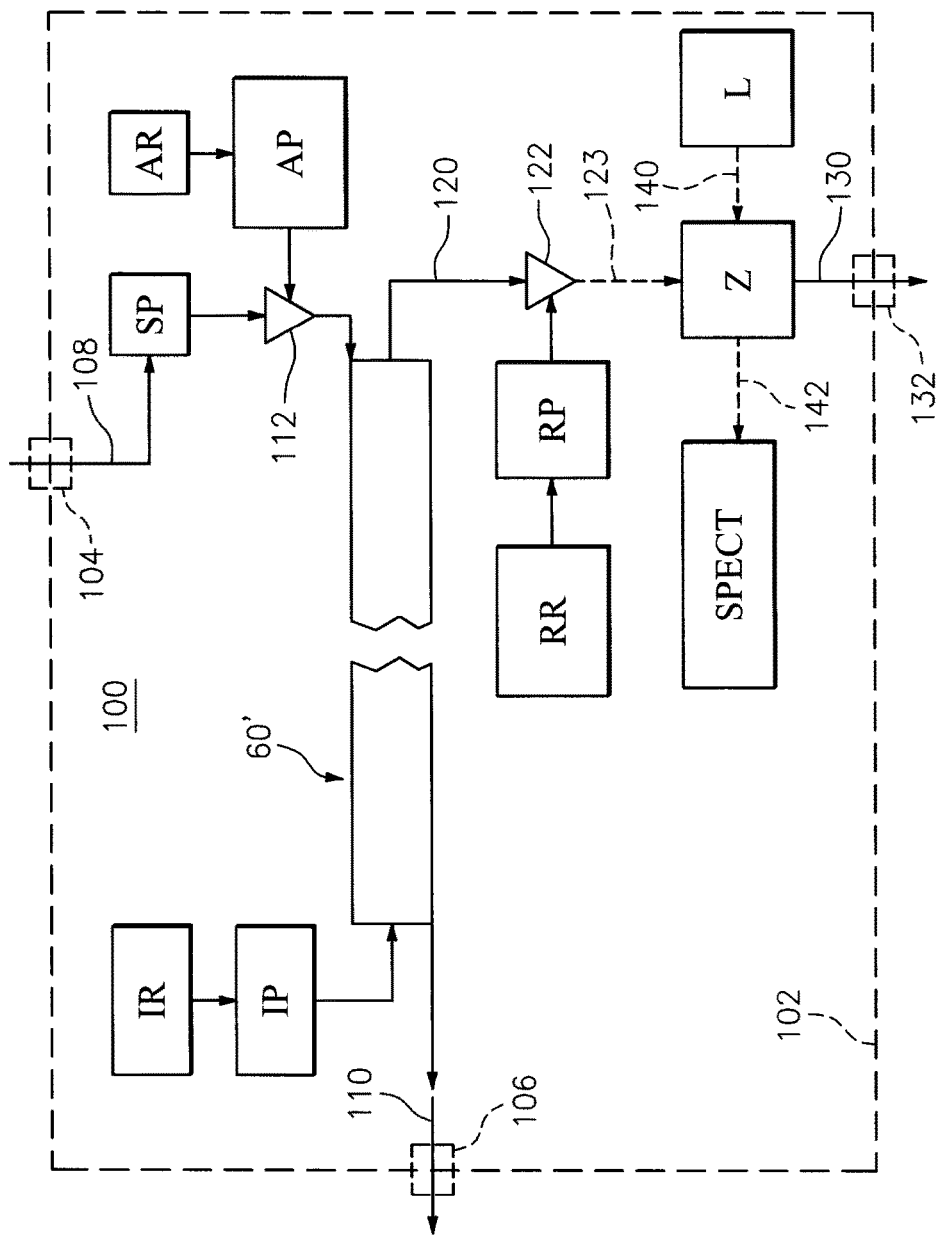
FIG. 2A is a schematic block diagram of a system according to the present invention utilizing countercurrent flow.

This invention may be accomplished by systems and methods that rapidly and at least substantially continuously measure at least one pre-selected dissolved gas, such as dissolved carbon dioxide or any suitable measurable substance which provides a colorimetric or detectable chemical change dependent on substance concentration or suitable gas utilizing a gas/liquid equilibrium (e.g., carbon dioxide or ammonia), within a sample liquid such as freshwater or seawater obtained from a quantity of the liquid such as a pond, lake, stream, bay, or ocean. The system and method include selecting a sample processing cell having at least a first conduit defining a first passage with at least one gas-permeable wall (e.g., membrane) capable of passing at least the pre-selected dissolved gas from the sample liquid into a reagent fluid. The at least one gas-permeable wall substantially resists flow of the sample liquid therethrough, that is, it maintains liquid separation between the sample and reagent fluids. The system and method further include directing reagent fluid through the first conduit while moving the sample liquid and the reagent fluid relative to each other in one of a concurrent and a countercurrent flow relationship to achieve either partial (e.g., at least 10%, at least 20%, at least 30%, at least 40%, or more preferably at least 50% equilibrium) or full 100% equilibration between the sample liquid and reagent fluid to generate at least partially equilibrated reagent fluid in a substantially continuous manner. The quantity of the dissolved gas in the at least partially equilibrated reagent fluid is measured by spectrophotometry or other measurement techniques. The sample liquid is obtained at least substantially continuously from the quantity of the sample liquid while the sample processing cell is immersed in the quantity of sample liquid (either directly or via a chamber or housing filled with seawater, fresh water, oil, etc.). Measurement systems according to the present invention are suitable for installation and use in situ on AUVs, ROVs, gliders, profilers, and other mobile or stationary platforms for submerged or water surface deployments. Other embodiments of the inventive system are adapted for land in wet or dry conditions such as in a laboratory setting.

In certain constructions, the system and method include at least a second measurement channel to measure another parameter such as pH. Other parameters may include total alkalinity (TA), partial pressure of $CO_2$, ammonia, heavy metals, or other suitable substances. Examples are provided below for an in situ (i.e., in the location of sample acquisition) DIC-pH sensor, Channelized Optical System (CHANOS), also referred to as a Dual-channel Modularized Autonomous System (D-MAS), for spectrophotometric DIC and pH measurements according to another embodiment of the present invention.

Measurements according to the present invention preferably are conducted substantially in "real time", that is with minimal response time (preferably less than one minute for countercurrent flow, more preferably less than 30 seconds, most preferably less than 15 seconds, and truly continuously for concurrent flow with a time lag of less than five minutes) in obtaining meaningful readings of the target parameter, even in deep ocean, high-pressure conditions. Other than optionally treating the sampled water, such as with an acid to convert a targeted substance such as a carbonate species to the target gas, no poisoning, preserving or stabilizing of the samples is needed. In other embodiments, the sampled water is treated with one or more reagents for such purposes as preserving, treating, or otherwise altering the sample prior to or after measurement.

A sample processing cell 10, FIG. 1A, includes a first conduit 12, having at least one gas-permeable wall, within a second, surrounding conduit 14. In this construction, reagent fluid is introduced to one end of cylindrical first conduit 12, as indicated by arrow 16, and exits from the other end of conduit 12 as indicated by arrow 18. A second, preferably concentric, conduit 14 is bounded by connectors 20 and 22 defining openings 24 and 26, respectively.

For concurrent flow relative to flow arrows 16 and 18 of the reagent fluid, sample liquid is introduced through opening 24, as indicated by arrow 28, travels along the exterior of first conduit 12 as indicated by flow arrows 30 and 32, and exits through opening 26 as indicated by arrow 34. For countercurrent flow, sample liquid is introduced through opening 26, dashed arrow 40, flows along first conduit 12 as indicated by dashed arrows 42 and 44, and exits through opening 24 as indicated by dashed arrow 46. Sample processing cell 10 has an effective transfer length L, indicated by arrow 50, representing the length over which dissolved gas equilibrates, that is, is transferred at least partially, from the sample liquid to the reagent fluid.

In one embodiment, as described by Z. A. Wang, S. N. Chu, and K. A. Hoering in "High-Frequency Spectrophotometric Measurements of Total Dissolved Inorganic Carbon in Seawater", *Environ. Sci. Technol.* 2013, 47 (14), 7840-7847 and shown in FIGS. 1B and 2A below, the spectrophotometric system and method according to the present invention achieve substantially continuous measurements of total dissolved inorganic carbon (DIC) in seawater. It uses a countercurrent flow design and a highly $CO_2$-permeable membrane (Teflon AF 2400) to achieve flow-through $CO_2$ equilibration between an acidified sample and an indicator solution with a fast response time of approximately 70 seconds for full equilibrium and approximately 22 seconds for 60%-70% partial equilibrium in one embodiment wherein indicator fluid has a transit time of approximately 10 seconds. This method improves the spatiotemporal resolution by more than one order of magnitude compared to the existing spectrophotometric method. The flow-through equilibration allows for continuous (~1 Hz) detection and real-time data smoothing. The method had a short-term precision of ±2.0 µmol kg$^{-1}$ for a given flow-through sample. It achieved a field precision of ±3.6 µmol kg$^{-1}$ and successfully captured high DIC variability down to minute scales. Measurements by the new method over the typical range of oceanic DIC showed good agreement with measurements made by an established method (mean differences −1.6-0.3 µmol kg$^{-1}$ with 1σ±6.0-6.7 µmol kg$^{-1}$). This level of precision and accuracy is comparable to that of the existing spectrophotometric method. The characteristics of the new method make it particularly suitable for high-frequency, submerged (e.g., partially or fully submerged) measurements required for mobile observing platforms in the ocean. It can also be adapted for high-frequency, spectrophotometric measurements of seawater $CO_2$ fugacity.

Described herein is a new spectrophotometric DIC method capable of attaining a much faster response time (e.g., about 22 s or less, less than 30 s, less than 1 min) using flow-through (dynamic) $CO_2$ equilibration by introducing countercurrent, continuous flow between the indicator solution and the liquid undergoing analysis, also referred to as the "sample", within sample processing cell 60, FIG. 1B. This new design allows for continuous measurements as compared to intermittent measurements made with the known, existing spectrophotometric method (referred to as the "intermittent method" hereafter). The new method according to the present invention (also referred to as the "continuous method" or "present method" hereafter) has achieved good measurement stability and repeatability, similar to those of the intermittent method. During field tests, the continuous method produced high temporal resolution DIC data that were in good agreement with measurements made by the established NDIR-based method. These characteristics make the continuous method particularly suitable for expanding observational capabilities of the $CO_2$ system on mobile observing platforms.

The intermittent spectrophotometric DIC method relies on 100% $fCO_2$ equilibration between acidified samples and a motionless indicator solution across the wall of Teflon AF tubing. After $fCO_2$ equilibrium, DIC (as total $CO_2$) of the acidified sample (denoted by subscript a) is proportional to $fCO_2$ of the internal indicator solution (denoted by subscript i):

$$\log(fCO_2)_a = \log\frac{[DIC]}{(K_0)_a} = \log(fCO_2)_i \qquad (1)$$

where $(K_0)_a$ is the Henry's Law constant for the acidified sample. The chemical and optical properties of the internal indicator solution can be expressed as:

$$\log(fCO_2)_i = B(t) - \log(K_0)_i - \log\left(\frac{R - e_1}{1 - Re_3/e_2}\right) \qquad (2)$$

such that:

$$\log\frac{[DIC]}{(K_0)_a} = B(t) - \log(K_0)_i - \log\left(\frac{R - e_1}{1 - Re_3/e_2}\right) \qquad (3)$$

$(K_0)_i$ is the Henry's Law constant for the internal indicator solution. The coefficients $e_1$, $e_2$, and $e_3$ are indicator molar absorbance ratios at wavelengths $\lambda_1$ and $\lambda_2$, where $\lambda_1$ and $\lambda_2$ are the wavelengths for the absorbance maxima of the indicator acid (HI$^-$) and base (I$^{2-}$) species. These coefficients are laboratory determined optical constants. R is the ratio of the indicator absorbance (A) measured at wavelengths $\lambda_1$ and $\lambda_2$, $R = _{\lambda_2}A/_{\lambda_1}A \cdot B(t)$ can be expressed as:

$$B(t) = \log(TA + [H^+] - [I^{2-}])_i + \log\left(\frac{K_I e_2}{K_1'}\right)_i \qquad (4)$$

where TA is the alkalinity of the indicator solution; [H$^+$] is the internal proton concentration; $K_I$ is the indicator dissociation constant; and $K_1'$ is the carbonic acid first dissociation constant for the internal solution. B(t) describes the chemical and optical properties of the indicator solution. It is an experimentally derived constant for a given temperature, calibrated using Certified Reference Material (CRM) obtained from A. G. Dickson at Scripps Institution of Oceanography.

For this work, Equation 3 has been re-arranged from the expression in the intermittent method by combining $(K_0)_a$ with the DIC concentration such that all sample-related terms are on one side of the equation, while all indicator-related terms are on the other. Bromocresol purple was used as the pH indicator, where $\lambda_1$=432 nm and $\lambda_2$=589 nm. A non-absorbing reference wavelength ($\lambda_{ref}$=700 nm) was used to correct baseline drift in absorbance measurements. The governing equations or values for all of the constants and coefficients in Equations 1-4 were previously described by Byrne and colleagues. Equation 3 quantitatively links DIC and $fCO_2$ in the acidified sample to $fCO_2$ and pH of the internal indicator solution at full $CO_2$ equilibration.

To make high-frequency DIC measurements possible, the new continuous DIC method uses a dynamic, partial equilibration process instead of a static, full equilibration which occurs in the intermittent method. A countercurrent flow design 60, FIG. 1B, was adopted to maintain fast and stable $CO_2$ exchange between the indicator and acidified sample. Countercurrent flow has been found extensively throughout nature in biological systems, such as in lungs and fish gills and has been imitated in engineering applications to achieve the maximum transfer of heat or chemicals. In this case, it maximizes the transfer rate of $CO_2$ between the indicator solution and samples.

In the continuous method, Teflon AF tubing was used only as a $CO_2$ equilibrator, not as both an equilibrator and a LCW as in the intermittent method. Other membranes or tubing may be used including silicone, bioabsorbable polymers or other suitable materials allowing high gas and low liquid permeability. As described in more detail below in relation to FIG. 2, optical detection occurs in an optical 'Z' cell after the indicator solution passes through the Teflon AF tubing of FIG. 1B. As the indicator solution travels the length of the Teflon AF tubing, partial $CO_2$ equilibration is attained between the indicator solution and the acidified sample. For a given sample, if such an equilibration process is repeatable each time the indicator solution passes through the Teflon tubing, and the optical detection is stable and sensitive, then the method can achieve continuous, high-quality DIC measurements. If desired, a slow indicator flow rate, combined with a long piece of Teflon AF tubing, will allow the indicator solution to reach 100% $CO_2$ equilibration.

The countercurrent flow design allows for dynamic, efficient exchange of $CO_2$ across the gas permeable tubing. If the indicator flows at a fast speed, by the time it reaches the end of the flow cell it has attained partial $CO_2$ equilibration with an exchange efficiency or percentage of equilibration, p (value 0-1), which can be included in Equation 3 to describe the continuous method:

$$\log\left(p \times \frac{[DIC]}{(K_0)_a}\right) = B(t) - \log(K_0)_i - \log\left(\frac{R - e_1}{1 - Re_3/e_2}\right), \quad (5)$$

where $$\log(p \times fCO_2)_a = \log\left(p \times \frac{[DIC]}{(K_0)_a}\right).$$

In Equation 5, the right side still represents $(fCO_2)_i$ while p is added to the left side of the equation to characterize partial $fCO_2$ equilibration. The variable p is used to characterize the equilibration process and is affected by operational conditions such as flow rate, temperature, indicator composition, and the $fCO_2$ gradient between the internal indicator solution and the external sample. It can be empirically built into the calibration and does not need to be explicitly defined for actual measurements. When p=1, Equations 3 and 5 are equivalent.

System 100 according to one embodiment of the present invention, FIG. 2A, is submersible in some constructions and, in other constructions, has one or more components that are not submersible. For submersible constructions, system 100 preferably is located within at least one water-tight housing 102 having ports 104 and 106, all depicted in dashed lines, for sample liquid intake, arrow 108, and sample outflow, arrow 110, respectively. Certain components such as valves and pumps preferably are contained in one or more oil-filled chambers to minimize the effects of changes in ambient pressure while maintaining separation from potentially corrosive sample liquids such as seawater, as will be familiar to those skilled in submersible technologies. In some embodiments, an oil such as a hydraulic oil (e.g., Royal Purple #7), a mineral oil, a synthetic oil, a composition of oils or other pressure-resistant fluid which comprises a compressibility of less than 10%, preferably less than 5%, and more preferably less than 1% per thousand meters water is used to fill the chambers within the system. The sample liquid 108, such as seawater, is drawn in by sample pump SP and is mixed at a valve 112 (e.g., T-type valve) with acid delivered from acid reservoir AR via acid pump AP. In this construction, the acidified sample is passed through a sample processing cell 60' in a countercurrent relationship to indicator liquid delivered from indicator reservoir IR via indicator pump IP. Countercurrent flow cell 60' is similar to sample processing cell 60, FIG. 1B.

After the indicator liquid is exposed to the pre-selected dissolved gas in the acidified sample stream within cell 60', the at least partially equilibrated indicator liquid 120 is directed through an optical "Z" cell Z and exits as waste stream 130, through port 132, for disposal. System 100 preferably includes a reference fluid for calibration of the measuring sensor or instrument such as a spectrophotometer SPECT. In one construction, fluid delivery to cell Z is alternated by a T-type valve 122 (or other multiport flow controlled entry) between the equilibrated indicator liquid 120 and a reference liquid from reference reservoir RR via reference pump RP for optical baseline measurements before and/or after indicator measurements. In another construction, reference liquid is delivered directly to cell Z as indicated by dashed line 123, and valve 122 is a simple flow control valve solely for the at least partially equilibrated indicator liquid 120.

Optical radiation is delivered from lamp L to optical cell Z via a fiber optic cable 140 or other waveguide. After the optical radiation passes through the indicator or reference liquid in optical cell Z, it is directed to a spectrophotometer SPECT via a fiber optic cable or other waveguide 142. Power to operate the pumps, lamp and spectrophotometer units can be obtained from the platform which carries system 100, from a separate battery pack within system 100, or from batteries within the individual units themselves. One or more controllers (not shown) are provided to control the operation of the pumps and valves.

In one construction, the continuous DIC measuring system 100, FIG. 2A, includes four high-precision digital peristaltic pumps (Ismatec® SA, Switzerland) for pumps SP, AP, IP and RP, a micro-volume, 10 mm optical 'Z' cell (SMA-Z-10-uvol; FIAlab Instruments Inc.) for optical cell Z, an Ocean Optics USB4000 spectrometer for spectrophotometer SPECT, and a white LED light source (LE-1W-CE; WT&T Inc., Canada) for lamp L. Other metering pumps or pump models tested for volumetric precision are also suitable. The countercurrent flow cell 60' was assembled with a 120 cm piece of Teflon AF 2400 capillary tubing (0.5 mm O.D. by 0.4 mm I.D.) and various commercial PEEK fittings and tubing (1.6 mm O.D. and 0.5-1.0 mm I.D.; Upchurch Scientific). In some embodiments, the capillary tubing is less than 120 cm in length, in one embodiment less than 100 cm and, in another embodiment, less than 50 cm in length. In other cases, a capillary tube greater than 120 cm is desired.

Figure 2B:
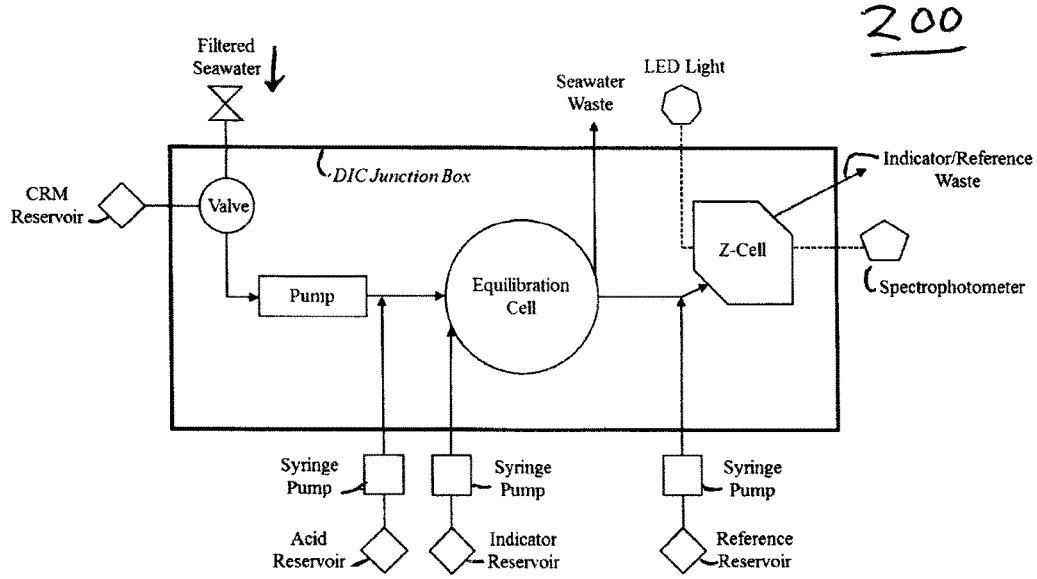
FIG. 2B is a schematic block diagram of a DIC channel of an in situ DIC-pH sensor system of FIG. 2D, referred to herein as a Channelized Optical System (CHANOS) or Dual-channel Modularized Autonomous System (D-MAS), for spectrophotometric DIC and pH measurements according to another embodiment of the present invention.

Additionally, the capillary tubing may be decreased in diameter to less than 0.4 mm internal diameter, or in some cases increased to an internal diameter greater than 0.4 mm up to 1 mm or more. For the results depicted in FIGS. 3-8B, the optical signals were monitored and recorded using a laptop PC and the Ocean Optics SpectraSuite software. The system 100, with all of its reagents and fluid (e.g., seawater) samples or standards, was thermostated at 25.0±0.1° C. with a water bath and a custom-made, air-circulated Peltier device. Flow-through seawater was pumped through a PEEK tubing coil to facilitate temperature equilibration. In some constructions, the system 100 performs measurements at a range of temperatures including less or equal to than 0° C., less than 10° C., less than 25° C., greater than 25° C., and in some cases up to or greater than 100° C. Additionally, the system may operate in an unregulated internal temperature environment. In some constructions, system 100 or system 200, FIG. 2B, are part of a larger system 400, FIG. 2D.

Figure 2C:
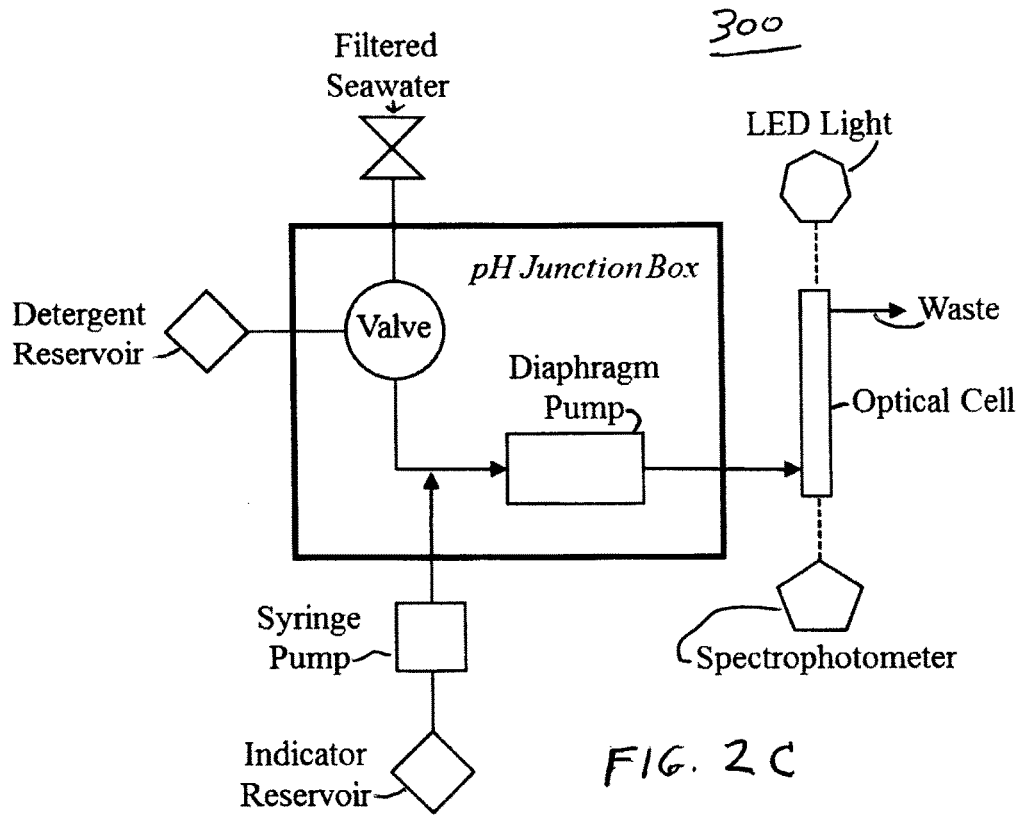
FIG. 2C is a schematic block diagram of a pH channel of the in situ DIC-pH sensor, dual-channel system of FIG. 2D.

The CHANOS pH channel 300, FIG. 2C, uses a flow-through design in which seawater or other sample liquid directly and continuously mixes with an indicator solution. It is based on the well-established spectrophotometric pH method, where dissociation of the added sulfonephthalein indicator ($H_2I$) in seawater is dominated by $$HI^- \xrightleftharpoons[]{K_I} H^+ + I^{2-};$$

$K_I$ is the dissociation constant of the indicator acid species $HI^-$. Combining Beer's Law, seawater pH can then be expressed as:

$$pH = pK_I + \log\frac{R - e_1}{e_2 - Re_3}, \quad (6)$$

where $R = {}_{\lambda_2}A/{}_{\lambda_1}A$, and $\lambda_1$ and $\lambda_2$ are the wavelengths for the absorbance maxima of $HI^-$ and $I^{2-}$; $e_1$, $e_2$, and $e_3$ are indicator molar absorbance ratios at wavelengths $\lambda_1$ and $\lambda_2$:

$$e_1 = \frac{\lambda_2 \epsilon_{HI}}{\lambda_1 \epsilon_{HI}}, e_2 = \frac{\lambda_2 \epsilon_I}{\lambda_1 \epsilon_{HI}}, e_3 = \frac{\lambda_1 \epsilon_I}{\lambda_1 \epsilon_{HI}}, \quad (7)$$

where $\lambda_1\epsilon_I$ and $\lambda_2\epsilon_I$ are the molar absorbances of $I^{2-}$ at wavelengths $\lambda_1$ and $\lambda_2$, and $\lambda_1\epsilon_{HI}$ and $\lambda_2\epsilon_{HI}$ refer to the molar absorbances of $HI^-$ at wavelengths $\lambda_1$ and $\lambda_2$. The indicators used in this work included thymol blue sodium salt ($\lambda_1$=435 nm and $\lambda_2$=596 nm) and m-cresol purple sodium salt ($\lambda_1$=434 nm and $\lambda_2$=578 nm), but may be any suitable pH indicator or colorimetric reagent. A non-absorbing wavelength (700 nm) was used to correct baseline changes. Calibrations of $pK_I$, $e_1$, $e_2$, and $e_3$ of the two indicators for typical seawater temperature and salinity have been established in laboratory experiments. It has been demonstrated that in situ spectrophotometric pH measurements require infrequent or no calibration.

Figure 2D:
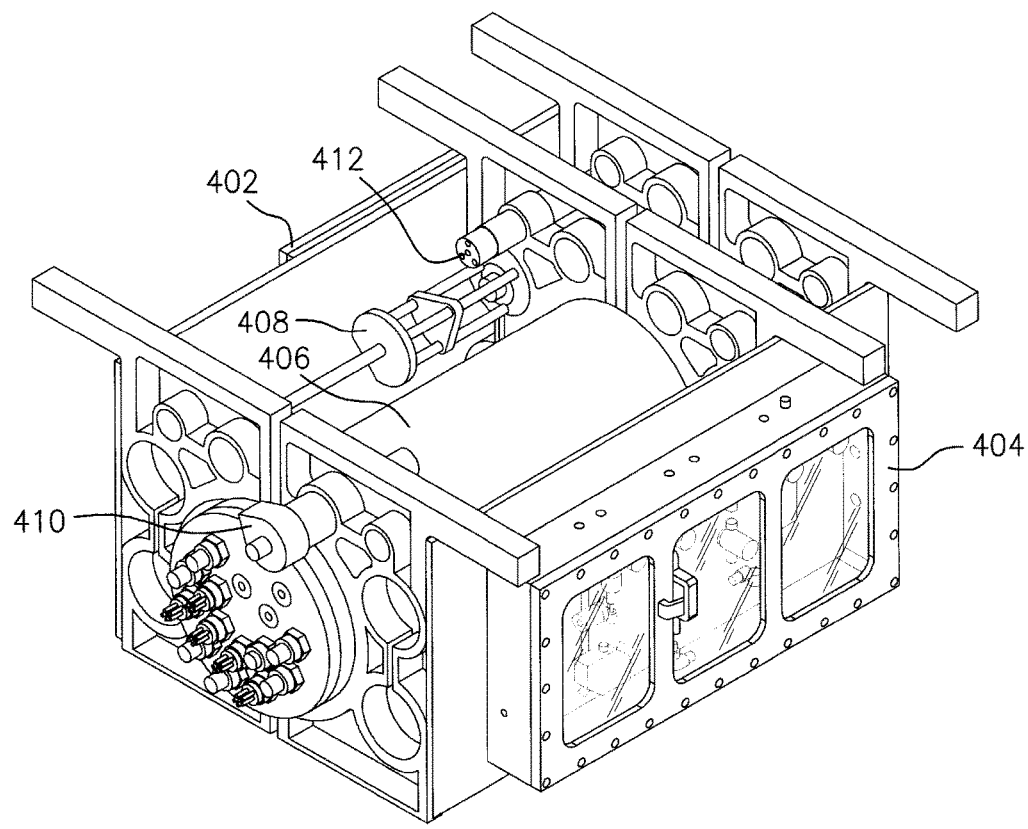
FIG. 2D is a schematic perspective illustration of the CHANOS which includes the channels depicted in FIGS. 2B and 2C.

In one construction, CHANOS 400, FIG. 2D, consists of four major components: two junction boxes (J-boxes) 402 and 404, one for pH and one for DIC, respectively, a pressure housing 406, four custom-made stepper-motor syringe pumps 408, and a Seabird pump 410 such as a Model 5P. Each J-box 402, 404 contains one 2-port and one 3-port solenoid valve (161K011, T161PK031, NResearch Inc.), a sample diaphragm pump (NF5, KNF Group International), thermistors, and optical and fluid handling components (FIGS. 2B and 2C). J-box components and pH Optical Cell 412 are described in more detail below. Infusion pumps, metering pumps, peristaltic pumps, syringe pumps or other pump models tested for pressure resistance and volumetric precision are also suitable.

The pressure housing 406 contains all of the controlling electronics, light sources, and the primary optical detection system. The controlling software runs on TERN microprocessors as described in more detail below.

Four custom-made syringe pumps 408 were made using high precision stepper motors (Phytron, Model ZSS 25-GPL26). In one construction, a Seabird pump 410 is used to pump sample water through a coarse copper mesh filter (preferably mesh size 100 μm but may be less than 100 μm or in some cases greater or equal to 200 μm), and each channel then subsamples water through an additional copper mesh filter (preferably mesh size 40 μm but may be less than 40 μm, less than 80 μm, or less than 100 μm) to reduce fouling within the system. Although other filters may be used, the copper filter is particularly adapted for the marine environment, resisting fouling on the filter itself. In some embodiments, the filter is coated with an anti-fouling coating. Discrete bottle measurements confirmed that there was no detectable difference between mesh-filtered and non-filtered samples for local coastal waters (mean difference 1.6±3.5 μmol kg$^{-1}$, n=9).

Figure 14A:
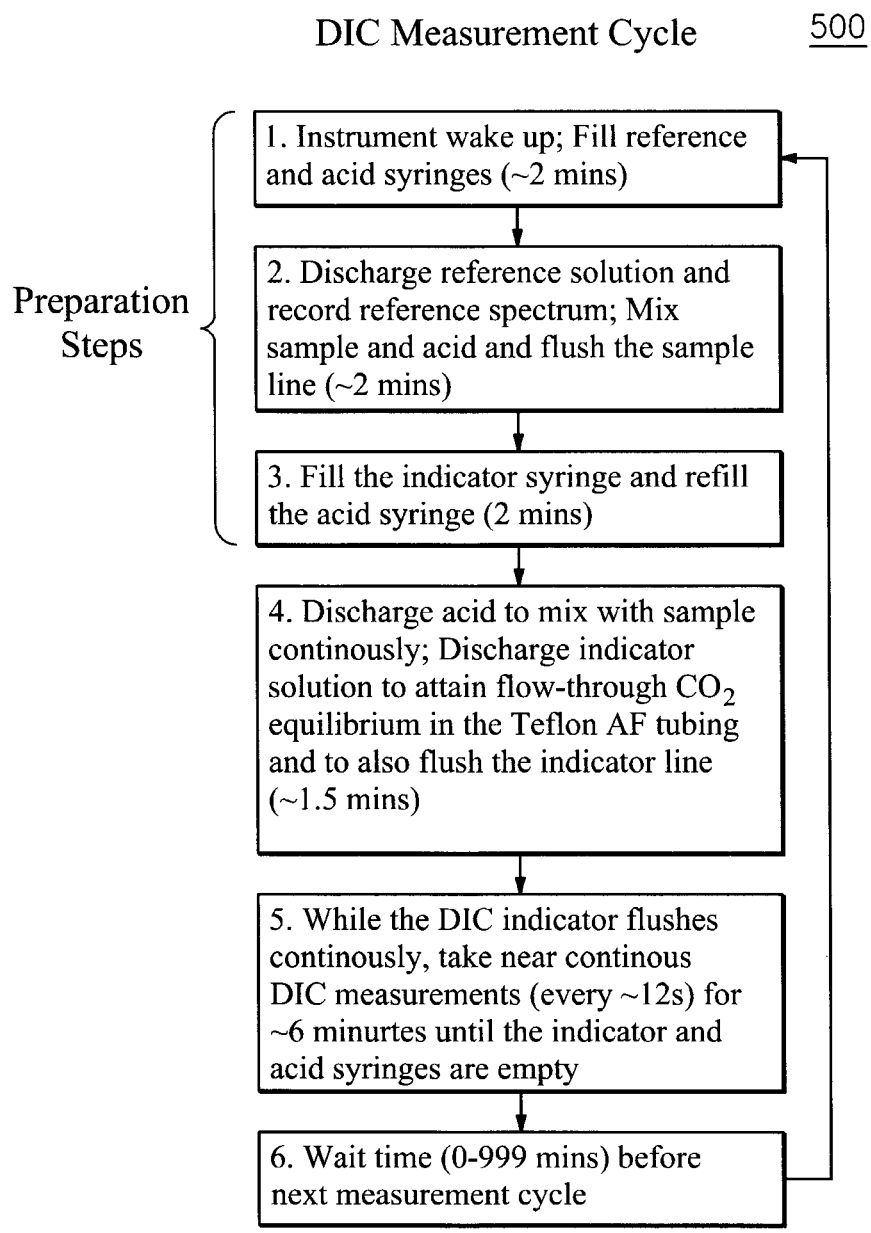
FIGS. 14A and 14B are flow charts of customizable DIC and pH running cycles for CHANOS.
Figure 14B:
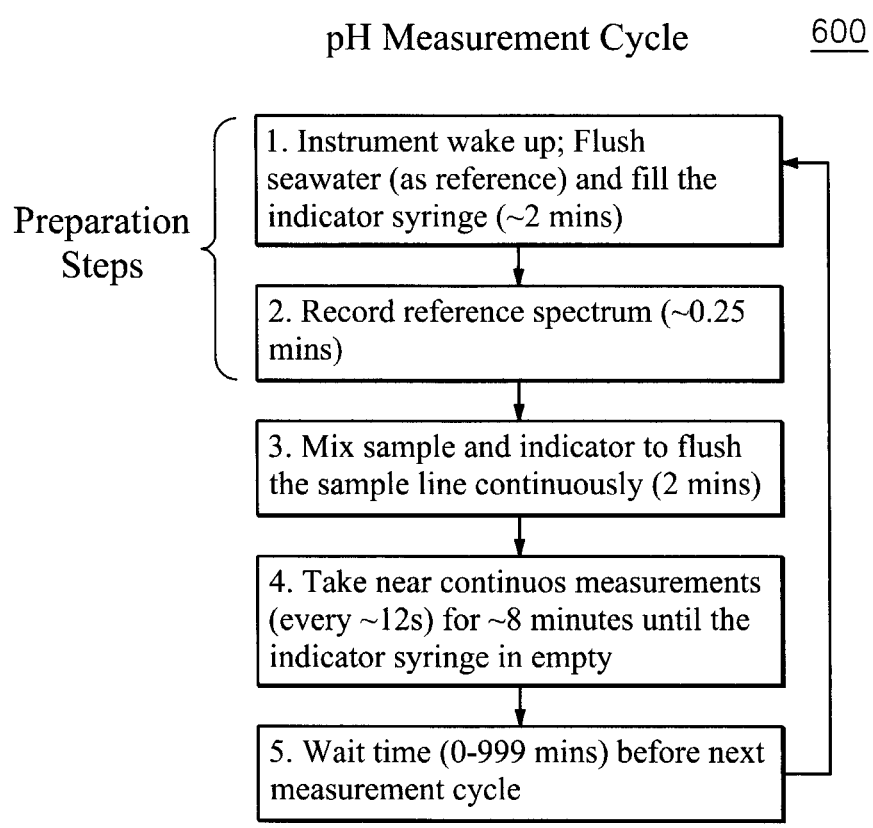

CHANOS runs on repeatable cycles, which include a series of mission steps for both channels as discussed in more detail below regarding FIGS. 14A and 14B. For the DIC measurement cycle, measurement preparation steps include filling the acid, reference, and indicator syringes, flushing the acidified sample and reference, and recording a reference spectrum (FIGS. 14A and 14B). Thereafter, indicator flows continuously through the Z-cell while acid continuously mixes with sample water and flows through the sample line until the indicator and acid syringes are emptied. Stable readings are achieved after the indicator has flowed for approximately 90 seconds. Thereafter, the system records approximately 6 minutes of spectra with near continuous DIC measurements (less or equal to about 12 s per measurement). Changes in the measurement cycle and size of the syringes can allow for higher resolution measurements as discussed in more detail below. The cycle is similar for in situ calibration, except that CRM is used in place of an external sample (FIG. 2B). For the pH channel, similar preparation steps take place before near continuous measurements (less or equal to about every 12 s for about 8 minutes) commence (FIGS. 14A and 14B). At a selected or pre-determined interval (e.g., once per day, or every few days), the pH channel is flushed with a Triton 100 detergent solution for cleaning purposes and reduce fouling within the system. For both channels, all steps are customizable depending on deployment purposes.

For DIC reagents, bromocresol purple ("BCP") sodium salt (Sigma-Aldrich) was used to make 4 mM indicator stock solutions that were stored in opaque glass bottles at 4° C. Working indicator solutions were prepared from the indicator stock solutions with a final concentration of 20-30 μM. This concentration, about 10 times that of the previous work (2-3 μM), was required to produce optimal absorbances with the short pathlength 'Z' cell. The alkalinity of the indicator solutions was established by adding extra-pure $Na_2CO_3$ (Acros Organics). Final TA concentrations of ~700-800 μmol kg$^{-1}$ were chosen so that the final indicator pH for measurements of typical seawater DIC concentrations fell within the range of ~5.6-6.4, where the indicator absorbance change is sensitive. This is similar to what has been achieved in the intermittent method. For each liter of indicator solution, 0.5 ml of 10% lauryl sulfate sodium salt solution was added to serve as a surfactant for cleaning purposes. Reference solutions were prepared using an identical procedure to the indicator solutions but without added indicator. The working indicator and reference solutions were enclosed in 2 liter gas-impermeable laminated bags (Calibrated Instruments, Inc.). Bagged solutions can last several months without any appreciable changes in composition. Hydrochloric acid (HCl, 2.5M) was used to acidify the samples.

Sodium carbonate solutions and Certified Reference Materials (CRMs) were used as DIC standards. The former were made with ultra-purified sodium carbonate (Sigma-Aldrich) in appropriate ionic strength sodium chloride solutions corresponding to various seawater salinities. They were stored in 1 L borosilicate glass bottles and poisoned with saturated mercuric chloride ($HgCl_2$). The DIC values of these standards were ascertained to within ±2.0 µmol kg$^{-1}$ using a NDIR-based DIC auto-analyzer (AS-C3, Apollo SciTech) that was calibrated with CRMs. The DIC concentrations were corrected for the dilution effect of $HgCl_2$ and density. CRMs were also stored in 2 liter gas-impermeable laminated bags (Calibrated Instruments, Inc.) used for in situ calibrations.

The NDIR-based DIC analyzer (AS-C3, Apollo SciTech) uses an inert gas (nitrogen) to purge $CO_2$ gas from a known amount of acidified seawater sample; the $CO_2$ in the resulting gas stream is quantified by a NDIR $CO_2$ analyzer (LI-7000, LI-COR). The calibration of the analyzer was conducted using CRMs on a twelve-hour interval. This instrument has a precision and accuracy of better than ±2.0 µmol kg$^{-1}$.

For the pH channel, thymol blue (TB) sodium salt (Sigma-Aldrich, ACS Certified) was used to make working indicator solutions with concentrations between 1.5-2.0 mM. TB is well suited for pH≥7.9 which is often observed in the local waters where the deployment occurred. The R ratio of the indicator solution was adjusted (R~0.77) to minimize indicator-induced pH perturbations. The pH indicator solution was also stored in a laminated bag. The sample-to-indicator mixing ratio was maintained at ~700:1, so that the final indicator concentration was approximately 2-3 µM. The indicator perturbation was generally smaller than ±0.002, and was corrected based on the standard procedure. The pH measurements were also corrected for the impurity of the indicators based on the recommended method through comparison with purified m-cresol purple (mCP) sodium salt.

The DIC measurement procedure is summarized as follows: (1) Seawater samples or DIC standards were acidified with HCl at a water-to-acid mixing ratio of ~700:1, and then directed to flow through the countercurrent flow cell outside of the Teflon AF tubing at a flow rate of ~4.0 mL min$^{-1}$ (FIG. 2A); (2) The optical cell was flushed with reference solution and a reference spectrum was taken; (3) Indicator solution was pumped at a selected flow rate, as described in more detail below, through the countercurrent flow cell (inside the Teflon AF tubing) in the opposite direction as the seawater, and the indicator solution exited the countercurrent cell after $CO_2$ exchange and flowed through the optical cell for absorbance detection at a frequency of ~1 Hz; and (4) Reference was retaken regularly to correct any potential absorbance baseline drift.

Calibration of the DIC system was necessary to establish a quantitative relationship between $$\frac{[DIC]}{(K_0)_a}$$

and $(fCO_2)_i$ under the selected running conditions. The CHANOS can make DIC measurements using either partial or full $CO_2$ equilibrium. If partial equilibrium is used for measurements, the calibration involved two steps for each batch of bromocresol purple indicator working solution. First, the system was calibrated with CRMs to obtain the B(t) constant in Eq. 5 by running the indicator solution at a slow speed (<0.03 mL min$^{-1}$), which allowed the indicator enough time (>5 minutes) inside the Teflon AF tubing to achieve 100% $fCO_2$ equilibration (p=1 in Eq. 3). B(t) was later used to calculate $(fCO_2)_i$ (the right side of Eq. 5) for standard runs at the higher selected indicator flow rate. Note that B(t) reflects chemical and optical properties of the indicator solution (Eq. 4), and does not change with indicator flow rate. Secondly, more than 5 DIC standards were measured at the same faster indicator flow rate to obtain the absorbance ratios in Eq. 5 corresponding to partial $fCO_2$ equilibration of each standard. $(fCO_2)_i$ was then calculated from Eq. 5 to establish a $(fCO_2)_i$ vs.

$$\frac{[DIC]}{(K_0)_a}$$

curve. Sample water was run at the same conditions as the DIC standards to obtain R. The sample DIC concentrations were calculated using B(t), R, and the calibration curve. In this procedure, the variable p is built into the calibration curve as described in more detail below. If full equilibration is used for measurements, only the first calibration step is conducted to obtain B(t).

Laboratory testing was conducted to establish calibration and measurement characteristics of the new method as well as to try to optimize running conditions. Thereafter, the continuous DIC system, FIG. 2A, was tested at the Environmental Systems Laboratory at Woods Hole Oceanographic Institution (WHOI), Woods Hole, Mass., USA for measurements of flow-through seawater that was pumped from a mile offshore. This test was conducted in June 2012 over three days. To groundtruth the new DIC method, traditional discrete DIC bottle samples were collected simultaneously with continuous DIC measurements. The samples were poisoned and measured using a NDIR-based DIC auto-analyzer. The new DIC system was further tested using discrete bottle samples that were collected from three hydrographic stations up to 3000 m in depth using a Conductivity-Temperature-Depth (CTD) Rosette Niskin Bottle package in August-September 2012 during a cruise in the North Pacific. The samples were collected in 1 L borosilicate glass bottles and poisoned with saturated mercuric chloride. Each sample was pumped through the DIC system for continuous measurements over a period of 15-20 minutes. Duplicate bottle samples were also collected into 250-ml borosilicate glass bottles following the same sampling procedure for the NDIR-based DIC measurements to gauge the new system's performance. All bottle samples were analyzed within two weeks.

A multi-channel system 400 according to another embodiment of the present invention, FIG. 2D, is an in situ DIC-pH sensor Channelized Optical System (CHANOS), capable of simultaneous spectrophotometric measurements of seawater DIC, FIG. 2B, and another parameter such as pH via a conventional pH sensor in system 300, FIG. 2C. The CHANOS is among the first sensor system that is able to fully resolve carbonate chemistry with a single system and a desirable pair of $CO_2$ system parameters measured to achieve small calculation errors. The CHANOS preferably has a build-in mechanism for in situ calibration, which ensures high measurement quality throughout a deployment and reduces the need for laboratory calibration. Preferably, the system is able to make high-resolution, climatology-quality measurements to resolve seawater-$CO_2$ system dynamics.

In one construction, the DIC channel portion of system 200, FIG. 2B, includes three custom-made high-precision stepper motor syringe pumps for the acid pump, the indicator solution pump and the reference fluid pump, a diaphragm pump for delivering the sample liquid to the equilibration cell, a micro-volume, 10 mm optical 'Z' cell (SMA-Z-10-uvol; FIAlab Instruments Inc.) for optical Z-cell, an Ocean Optics USB4000 spectrometer for spectrophotometer SPECT, and a custom-made white LED light source for lamp L. In one construction, the countercurrent flow cell is assembled with a 120 cm piece of Teflon AF 2400 capillary tubing (0.5 mm O.D. by 0.4 mm I.D.) and various commercial PEEK fittings and tubing (1.6 mm O.D. and 0.5-1.0 mm I.D.; Upchurch Scientific). The optical signals were monitored and/or recorded internally on a storage medium such as a flash drive using custom-made software.

The DIC Junction Box (black line box) with all its items are filled with a suitable conventional oil and sealed from the outside environment to provide protection and pressure compensation in water. The LED light, spectrophotometer, and all electronic components are placed in a water-tight pressure housing, such as housing 406, FIG. 2D. All custom-made syringe pumps are water-proof.

Figure 3:
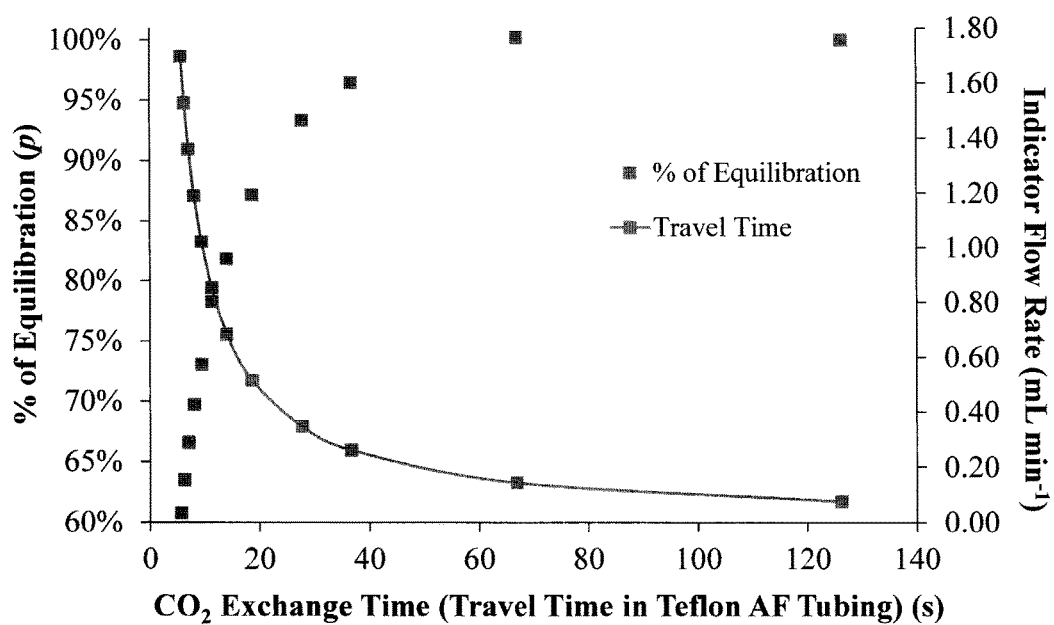
FIG. 3 is a graph showing the percentage of equilibration and indicator flow rate as a function of $CO_2$ exchange time.

Regarding measurement characteristics, FIG. 3, the percentage of $CO_2$ equilibration (p) is a function of indicator flow rate or travel time through the 120 cm long Teflon AF tubing for the systems of FIGS. 1B and 2A. Travel time is the amount of time that it takes for the indicator solution to travel the length of the Teflon AF tubing. This is also equivalent to $CO_2$ exchange time, the amount of time that the indicator solution exchanges $CO_2$ with the acidified sample. The variable p increases non-linearly with an increase in $CO_2$ exchange time. A higher indicator flow rate would allow for less travel time in the Teflon tubing for $CO_2$ exchange, resulting in lower $CO_2$ equilibration, faster response time, and greater indicator consumption. At very high flow rates, the optical detection becomes noisy probably due to increased pulsing from the peristaltic pump, causing unsteady flow in the optical cell. Travel time or $CO_2$ exchange time inside the Teflon AF tubing with a fixed internal volume is proportional to the reciprocal of indicator flow rate (FIG. 3). Bench-top testing utilized an indicator flow rate of ~1 mL min$^{-1}$, equivalent to a 9 s $CO_2$ exchange time, which is an effective balance between indicator consumption, response time, and detection stability. A further increase in indicator flow rate would not significantly decrease $CO_2$ exchange time. The system can reach 100% equilibration for a travel time of ~70 s, which is more than 4 time faster than the intermittent method.

Figure 4A:
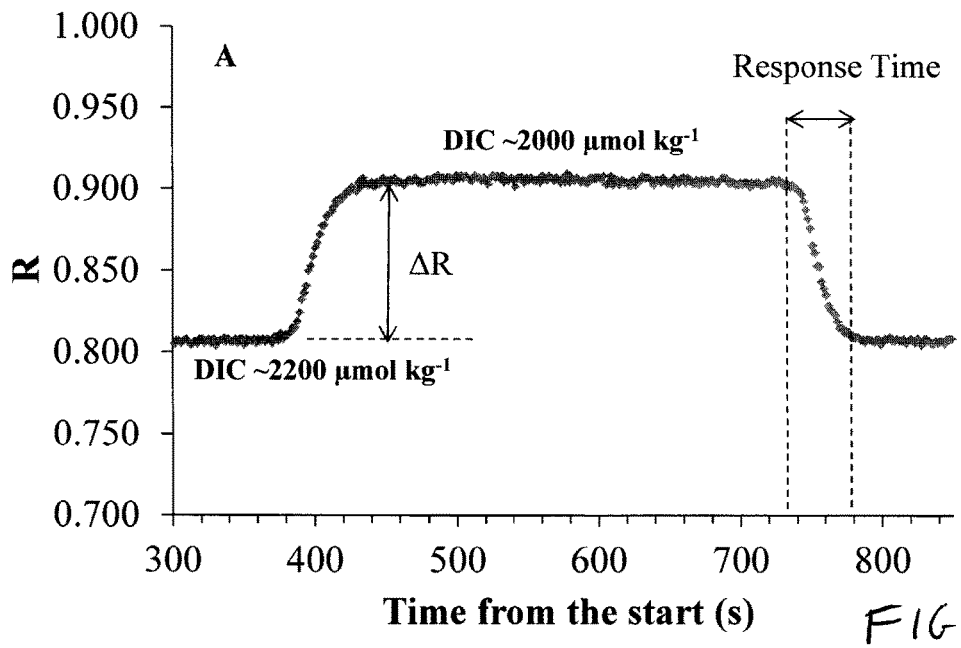
FIG. 4A is a graph of indicator solution response to absorbance ratio as a function of time, at the same running conditions as for FIGS. 4B-8B.
Figure 4B:
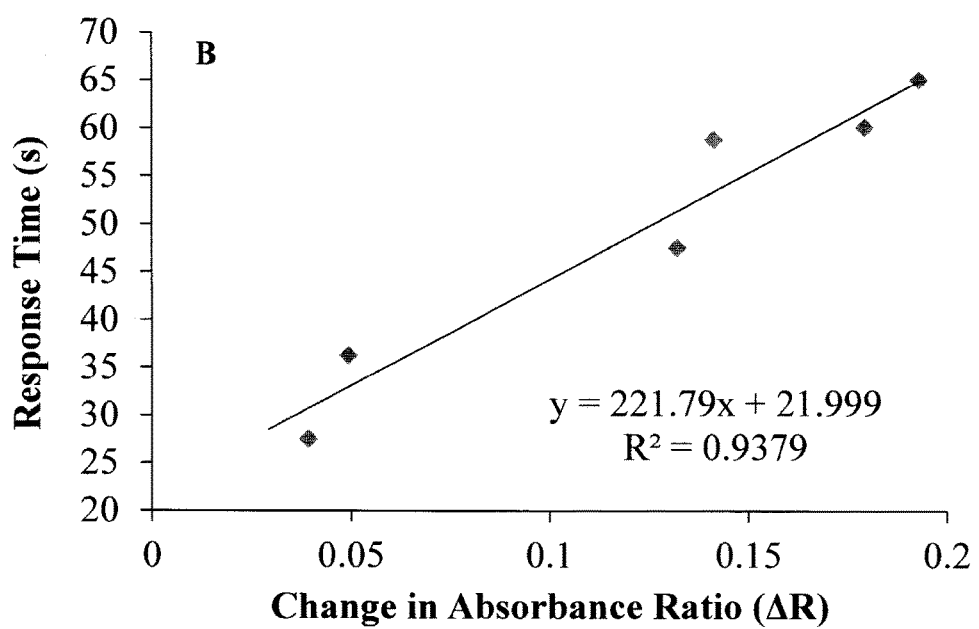
FIG. 4B is a graph of response time as a function of change in absorbance ratio.
Figure 5:
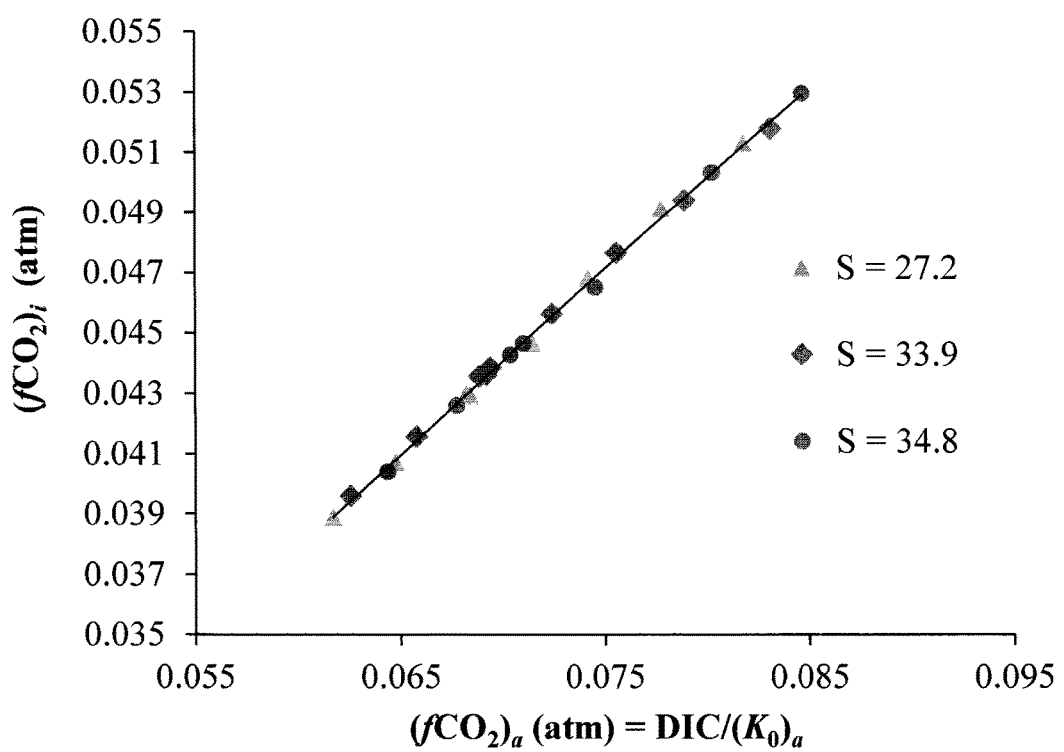
FIG. 5 is a graph of calibration data for DIC (Dissolved Inorganic Carbon) using standards with three different salinities.
Figure 6:
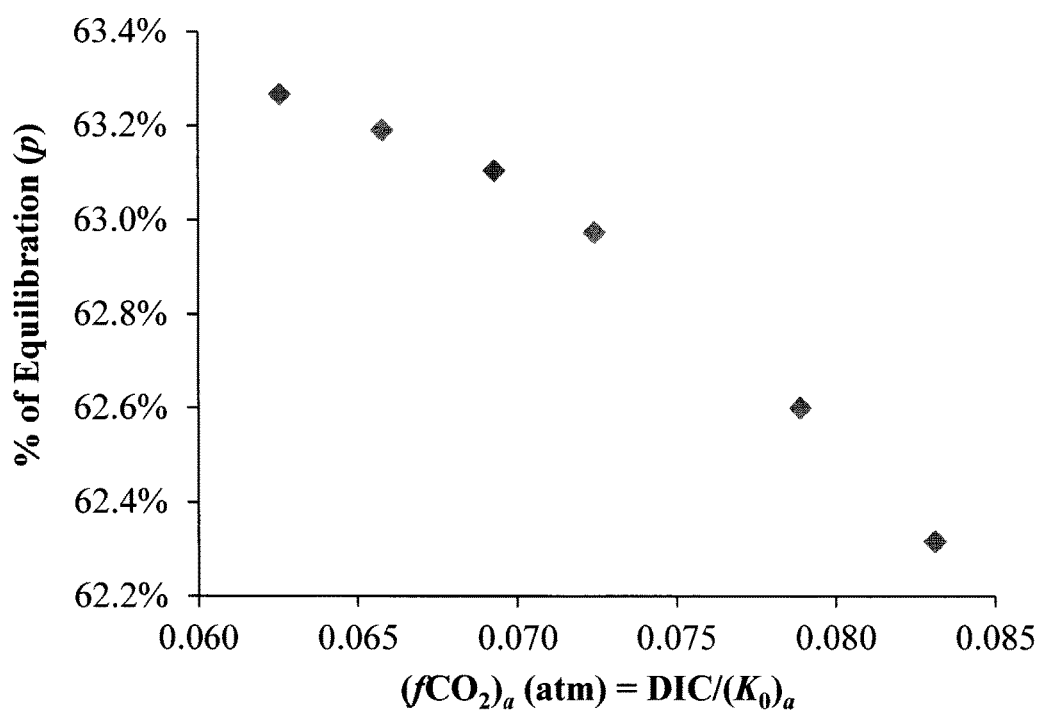
FIG. 6 is the percentage of equilibration across Teflon AF tubing as a function of $fCO_2$ in the acidified sample.

At the current settings with partial equilibrium, it takes approximately 35-60 seconds to achieve a steady response at 25.0° C. while varying between two samples with DIC concentrations in the range of approximately 1800-2400 µmol kg$^{-1}$ (e.g. FIG. 4A). The response time only varies by a few seconds for a given change in absorbance ratio under the same running condition. There is a significant linear relationship between response time and changes in absorbance ratios when switching between two DIC samples (FIG. 4B). The response time is much longer than the $CO_2$ exchange time of ~9 s under the current settings. The discrepancy between the two is likely due to the time that is required to flush the Teflon tubing and the optical cell with new indicator solution. Because of laminar flow throughout the flow path, the volume needs to be replaced several times before it is completely flushed. This explanation is consistent with the fact that the response time becomes shorter when AR, or the concentration difference between the two samples, decreases (FIG. 4B). The intercept in FIG. 4B thus approximately represents an actual response time of ~22 s during flow-through measurements, when sample concentration change is incremental as opposed to large changes as shown in FIG. 4A. The response time can be further improved by reducing the internal volume in the indicator flow path to reduce the effect of laminar flow.

The current response time (~22 s) is more than one order of magnitude faster than that in the intermittent method (~5 mins) with static, full equilibration. The data does not show that there is an apparent difference in response time between the countercurrent and concurrent flow under the current partial equilibrium settings. This may be because a large portion of the response time results from the time that it takes to flush the system. However, the countercurrent flow can achieve a slightly higher $CO_2$ diffusion efficiency by a few percentages for a 9 s $CO_2$ exchange time.

In the present method, the signal change for a 9 s $CO_2$ exchange time is ~92% of the total signal change if the indicator reached full equilibration. However, the same exchange time using static equilibration in the intermittent method only allows for ~65% of the total signal change. As such, the dynamic equilibration can achieve a 40% increase in equilibration efficiency as compared to static equilibration. It would take about 60 s with static equilibration to reach the same total signal change of 92%. Therefore, $CO_2$ equilibration in the continuous method is 6 times faster than that in the intermittent method. It is impractical to use partial equilibration in the intermittent method since the signal associated with a short exchange time (e.g. 9 s) would fall on a sharp changing slope, resulting in an unstable and inconsistent recording, and would have large measurement errors. For dynamic partial equilibration in the continuous method, a stable and consistent signal is reached before recording (FIG. 4A). Under the current settings, the variability in absorbance ratio (R) when measuring a stream of water with a constant DIC is only ~±0.0017 (1σ), which translates to a DIC analytical uncertainty (short-term precision) of ±2.0 µmol kg$^{-1}$.

Calibration curves for the continuous DIC method (FIG. 5) were derived over the DIC range encountered in samples with an indicator flow rate of 1.0 mL min$^{-1}$ and a sample flow rate of 4.0 mL min$^{-1}$ at a temperature of 25° C. The data in FIG. 5 were obtained from three series of calibrations at three different salinities using the same indicator solution and running conditions. Each series of calibration generates a polynomial equation, with a standard error of ±1.0-3.0 µmol kg$^{-1}$, comparable to the measurement precision (±2.0 µmol kg$^{-1}$). The effect of varying the salinity of the DIC standards has no measurable effect on the calibration curves in FIG. 5. This is because the salinity effect on (fCO$_2$), has been accounted for since (fCO$_2$)$_a$ was calculated from DIC values and (K$_0$)$_a$ (Eq. 1), and the latter is a known function of salinity. Internally, salinity for a given indicator solution is low (S~0.05) and constant. Beyond the effect on $(K_0)_a$, salinity did not have a measurable effect on the calibration curves in the salinity range encountered. Three individual calibration curves and the calibration curve containing all of the data in FIG. 5 had a pooled mean difference of 0.5±3.4 μmol kg$^{-1}$. This is within the 95% confidence interval of measurement uncertainties.

Under fixed running conditions with a particular indicator solution, the variable p is a function of the $fCO_2$ gradient between the acidified sample and the indicator solution. The slight convex of the calibration curve in FIG. 5, demonstrates that p varied over the $(fCO_2)_a$, or DIC, range (p represents the slope of the curve as defined in Eq 5). As $(fCO_2)_a$ in samples increases, p decreases under the same running conditions for the results shown in FIG. 6. This can be explained conceptually as follows: the $fCO_2$ gradient across the Teflon AF tubing increases as $(fCO_2)_a$ increases; for a given indicator flow rate (thus a fixed time for $CO_2$ exchange inside the Teflon AF tubing), p decreases with an increase in the sample-indicator $fCO_2$ gradient. However, this effect is relatively small at the selected running conditions (FIG. 6): p only changes by ~1.0% in the $(fCO_2)$, range corresponding to a DIC range of 1780-2370 μmol kg$^{-1}$. This effect can be fully accounted for in the system calibration using the curve of FIG. 5.

Figure 7A:
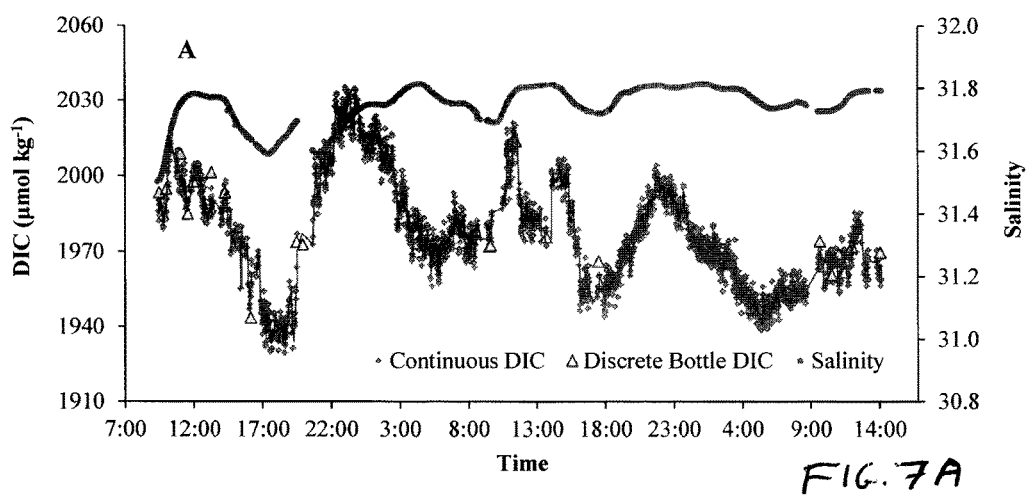
FIG. 7A is a graph of continuous seawater DIC measurements according to the present invention along with flow-through salinity and discrete DIC bottle measurements at different time periods.

Field testing conducted at WHOI Environmental Systems Laboratory was designed to demonstrate high-frequency, high-quality measurements using the new DIC method (FIG. 7A). During the 3-day period, which spanned multiple tidal cycles, salinity of the flow-through water varied slightly (31.5-31.8), while temperature showed ~4° C. variation (16.5-20.5). DIC concentration varied moderately (1929-2035 μmol kg$^{-1}$). Salinity and DIC sometimes showed a strong correlation, while at other times no correlation was observed, which suggests complicated tidal mixing. Each DIC data point in FIG. 7A represents a mean of 1-Hz measurements over one minute intervals. The measurements captured substantial variability on both short (minutes to a few hours) and longer (hours to days) time frames.

To evaluate the precision of the continuous DIC measurements during the testing, the data in FIG. 7A were smoothed by taking running averages (n=5; ~5 minute interval as indicated by the solid line within the continuous DIC measurements in FIG. 7A). The mean residual of individual observations relative to the running average was 0.1±3.6 μmol kg$^{-1}$ (N=2332). This uncertainty is likely an upper limit since the estimate includes DIC variability within a few minutes in the flow-through seawater, the variability that may occur in coastal oceans. It may explain the slightly lower precision in the field testing compared to that in the laboratory experiment. This estimated precision is comparable to that (~3.0 μmol kg$^{-1}$) of the intermittent method under field testing.

Figure 7B:
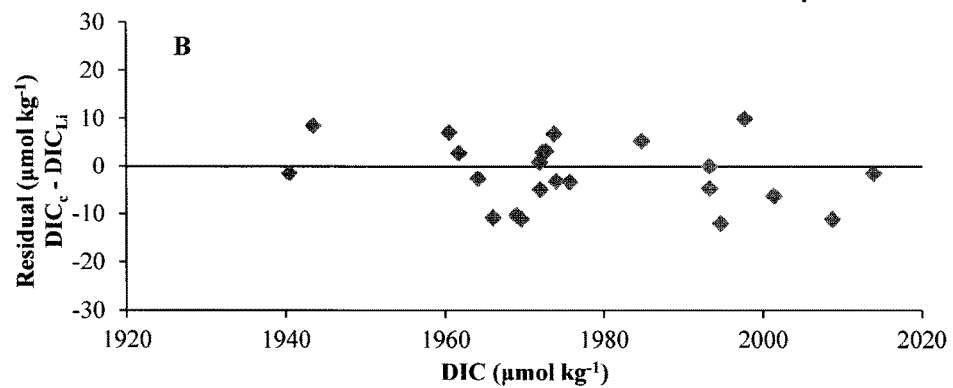
FIG. 7B is a chart of residuals between the continuous and discrete DIC measurements of FIG. 7A.

The accuracy of the continuous method was assessed by directly comparing the differences between continuous measurements and the NDIR-based bottle measurements (FIG. 7A). Both methods used standards traceable to CRMs for system calibration. Residuals between the continuous and the discrete bottle measurements did not show systematic trends (FIG. 7B). This suggests that any systematic errors in our measurements were minor. The continuous DIC measurements differ from the bottle measurements by −1.6±6.7 mol kg$^{-1}$ (N=23). Such accuracy is similar to that in previous development. The new method thus achieved high-frequency measurements as well as accuracy and precision comparable to the existing spectrophotometric method.

Figures 8A, 8B:
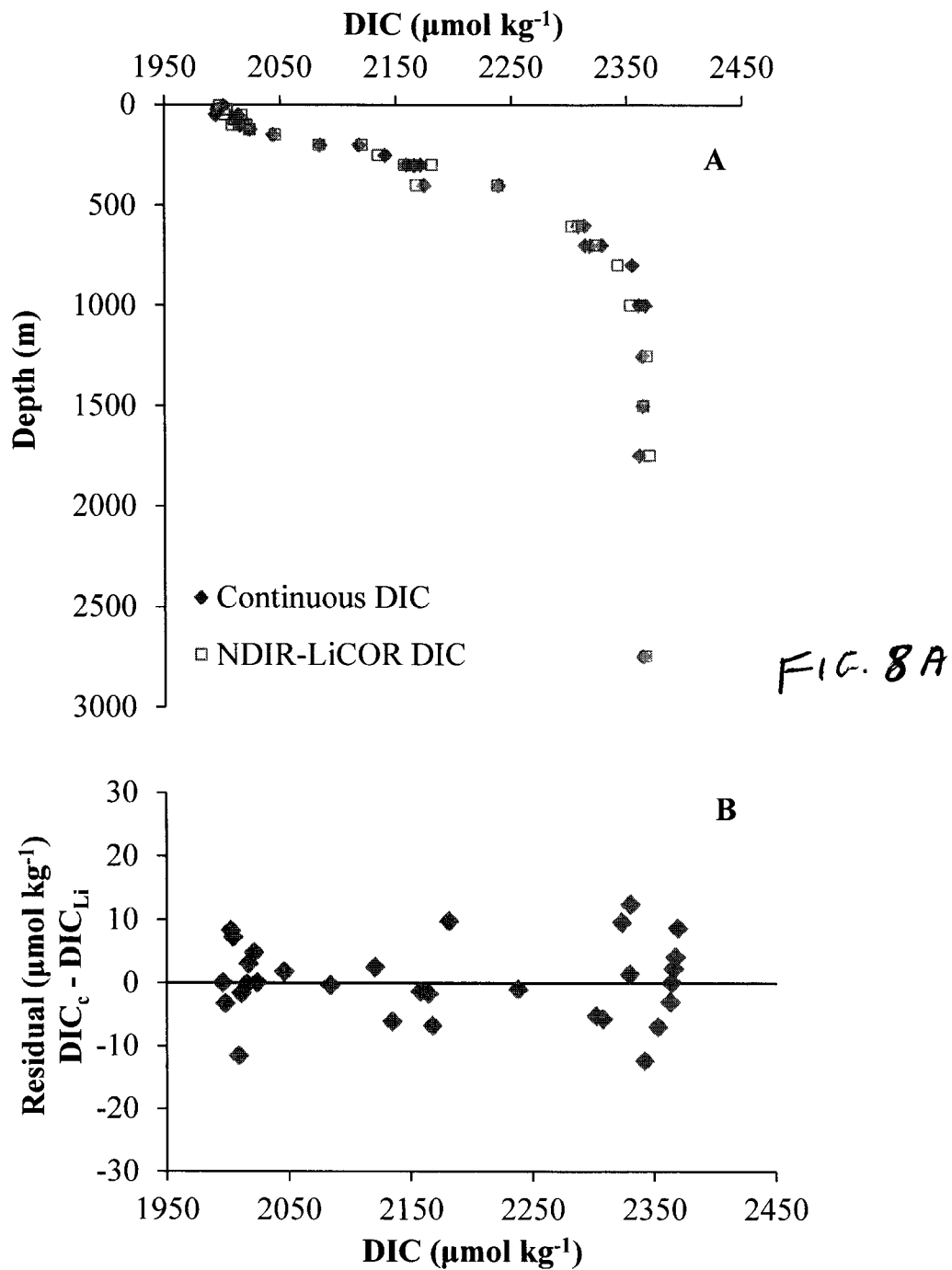
FIG. 8A is a graph of water-column DIC measurements by continuous and NDIR-based methods by depth.
FIG. 8B is a chart of residuals between the continuous and discrete DIC measurements of FIG. 8A.

The DIC system was also used to make measurements of discrete bottle samples collected from three stations in the North Pacific at depths up to 3000 m. This test effectively captured the large DIC concentration range that may be encountered in the ocean (FIGS. 8A and 8B). In this case, DIC concentration varied from ~1990 μmol kg at the surface to ~2370 mol kg$^{-1}$ at depth, a nearly 400 mol kg$^{-1}$ difference (FIG. 8A). The DIC measurements by the continuous method were also in good agreement with NDIR-based analyses. The mean difference between the two methods was 0.3±6.0 μmol kg$^{-1}$ (N=31). This level of accuracy is comparable to that achieved in high-frequency measurements shown in FIG. 7. No systematic errors were observed over the DIC measurement range, as evidenced by the random distribution of the residuals between the spectrophotometric and NDIR-based measurements (FIG. 8B). This test suggests that the new DIC method can attain good precision and accuracy over a wide range of seawater DIC concentrations and in submerged conditions.

The estimated field precision (±3.6 μmol kg$^{-1}$) was about 53-60% of the field agreement estimates (+6.0-6.7 μmol kg$^{-1}$; FIGS. 7A-8B). The measurement variability resulting from the inherent noise of the new DIC system therefore accounts for ~53-60% of the variability observed in FIGS. 7B and 8B. The rest of the variability may be attributed to various external sources. These may include discrete sampling and NDIR-based analytical uncertainties. It is important to note that the level of measurement uncertainty achieved with the continuous DIC method is comparable to those of replicate bottle sample measurements using conventional DIC methods during major carbon cruises (http://cdiac.ornl.gov/oceans/).

For the CHANOS, all previously calibrated constants for spectrophotometric pH measurements (Eqs. 6-7) can be used for CHANOS pH calculations. CHANOS was tested in situ for several months in Fall 2013 at the Iselin dock of the Woods Hole Oceanographic Institution (WHOI), Woods Hole, Mass., USA. The first several weeks were used to diagnose the overall functionality of the instrument and to make necessary changes. Thereafter, in situ measurements were made for three weeks. The sensor was programmed to make measurements every 40 minutes (FIGS. 14A and 14B). Although such a long wait time between measurements is not sufficient for capturing short time scale variability, it was sufficient for field testing.

The sensor, contained in a Pelican case, was hung in a testing well at ~5 m depth. The case provided protection to the sensor and reduced system fouling. A Seabird conductivity-temperature-depth (CTD) sensor (SBE 49) was also deployed with the sensor. A piece of Tygon tubing used for discrete sampling was co-located with the sensor sample intake for direct comparison. A field peristaltic pump was used to pump water onto the dock to collect discrete DIC and pH samples in order to assess sensor accuracy. Bottle samples were collected in 250 mL borosilicate glass bottles and poisoned with mercuric chloride following the standard procedure. Their measurements are described in Supporting Information.

The CHANOS pH channel has similar measurement characteristics as previously developed spectrophotometric pH sensors. The flow-through design allows for continuous pH measurements after taking reference spectra. The syringe pumps allow for precise delivery and therefore maintain a stable sample-to-indicator mixing ratio during long deployments. They also minimize indicator consumption. The self-cleaning mechanism for the pH sample line using detergent (FIG. 2C) effectively reduces fouling inside the sample tubing and maintains throughput light in the pH optical cell. During the three week in situ testing, the light level was only reduced by approximately 10%.

Figure 9:
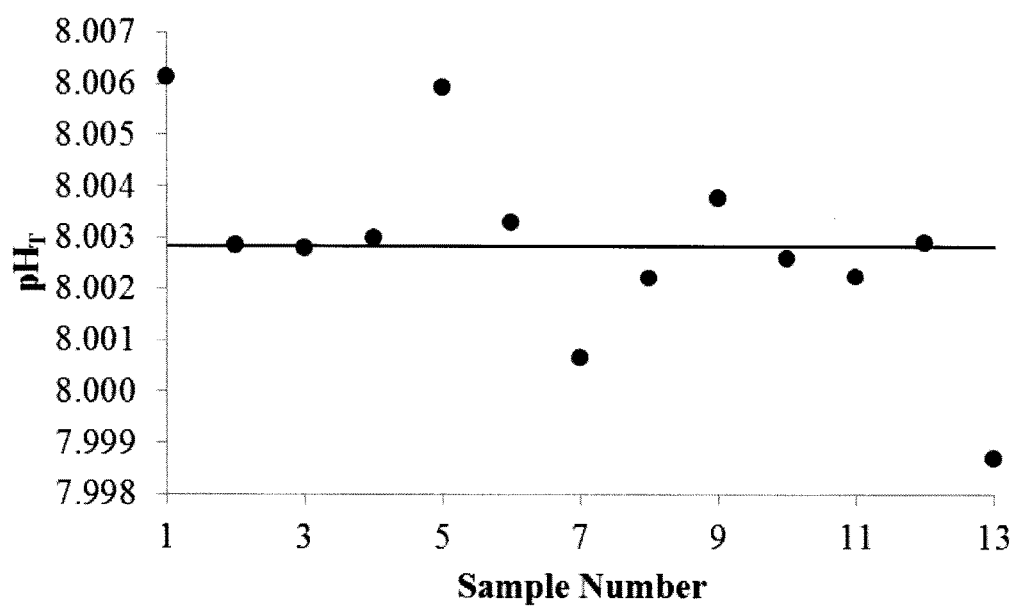
FIG. 9 is a graph of in situ repeated pH measurements of coastal waters.

Sensor performance was evaluated in the laboratory and during the field deployment. During laboratory experiments, spectra (n=15) recorded within a pH measurement cycle had a precision of ±0.0010 pH units (data not shown). Across measurement cycles (n=10) of the same sample, the CHANOS pH channel also achieved a precision (repeatability) of ±0.0010 pH units which is comparable to similar pH sensors. During the three-week field deployment, the precision of the pH measurements was ±0.0019 pH units (n=13) (FIG. 9) over repeated measurements during the last two minutes of a measurement cycle. This standard deviation is slightly larger than that found in the laboratory experiments, which suggests that there may be high variability in water chemistry at the testing site over a short time period. Overall, CHANOS showed good in situ pH repeatability.

Figure 10A:
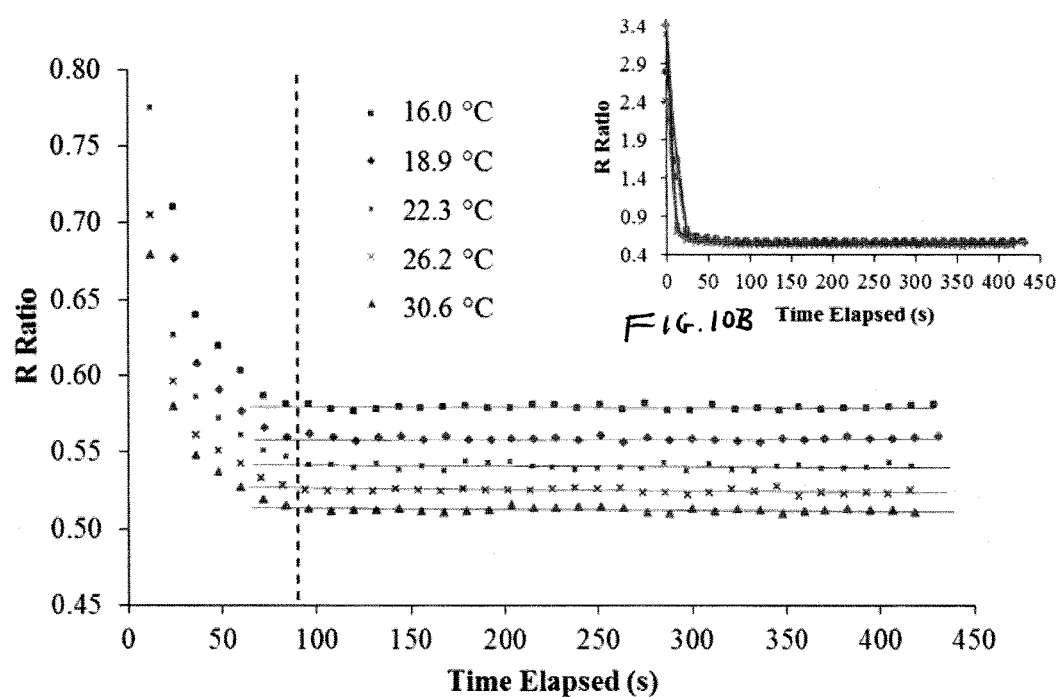
FIG. 10A is a graph of response time of DIC measurements at different temperatures.

The response time for CHANOS DIC measurements was at least 3 times faster than previous spectrophotometric measurements using a similar size of Teflon AF 2400 tubing. At the current settings, it takes ~90 s for fresh indicator solution to achieve a stable reading at 100% equilibration for samples with a DIC concentration of ~2000 mol kg$^{-1}$ (FIGS. 10A and 10B), compared to about 300 s in the previous development. Temperature had an insignificant influence on the response time for the current design based on lab experiments. Such insensitivity is expected as the response time herein reflects the time that it takes for the system to flush the indicator line with newly $CO_2$ equilibrated solution, which is not temperature dependent.

Currently, CHANOS makes DIC measurements using flow-through, full $CO_2$ equilibration and requires only calibration of a single operation constant B(t) (Eq. 4). The DIC measurement precision is +2.5 μmol kg$^{-1}$ as determined by repeated measurements, which is similar to previous underway and in situ systems (Table II below).

Figure 11A:
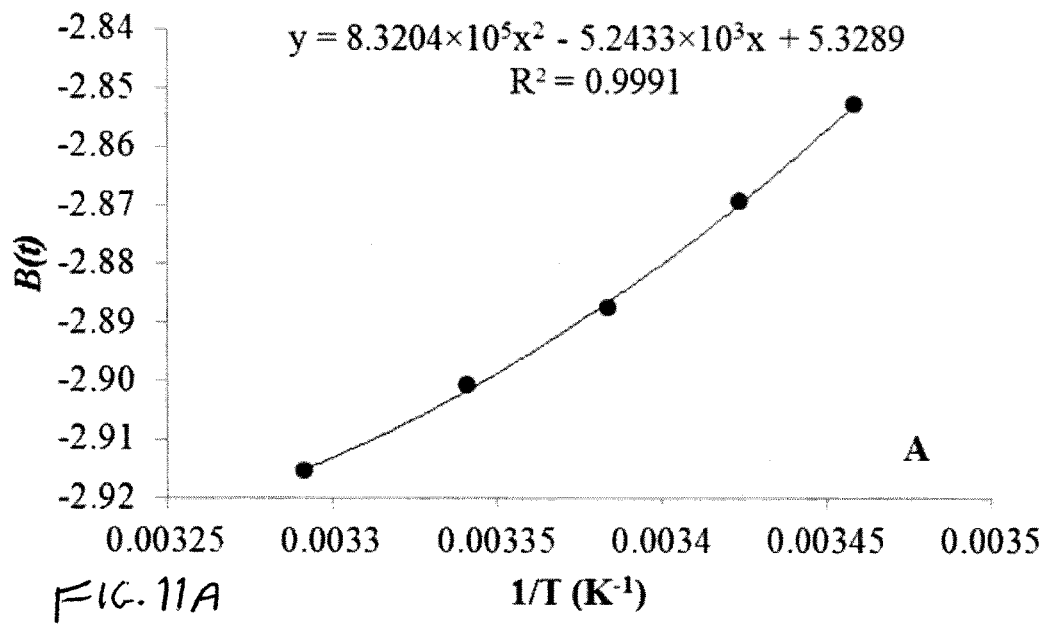
FIGS. 11A and 11B are graphs DIC calibration constant B(t) as a function of measurement temperature under laboratory and in situ conditions, respectively.

Calibration constant B(t) is a function of temperature as described by Eq. 4, where $K_f$, $e_2$, and $K_1'$ of the indicator solution are all temperature dependent (FIG. 11A). In theory, B(t) can be calculated using the knowledge of the indicator solution composition and thermodynamic constants via Eq. 4. However, the terms in Eq. 4 may have an overall uncertainty that exceeds the acceptable range for climatology-quality DIC measurements. The B(t)-temperature function was thus experimentally determined by measuring CRMs at different temperatures. Such a strategy is convenient as it does not require knowledge of all terms in Eq. 4, but results in well-constrained uncertainties in DIC measurements. The mean difference in B(t) between measured and predicted values based on the best-fit curve in FIG. 11A can be translated to a DIC error of 0.4±2.7 μmol kg$^{-1}$, which is similar to the uncertainty in repeated measurements.

Figure 11B:
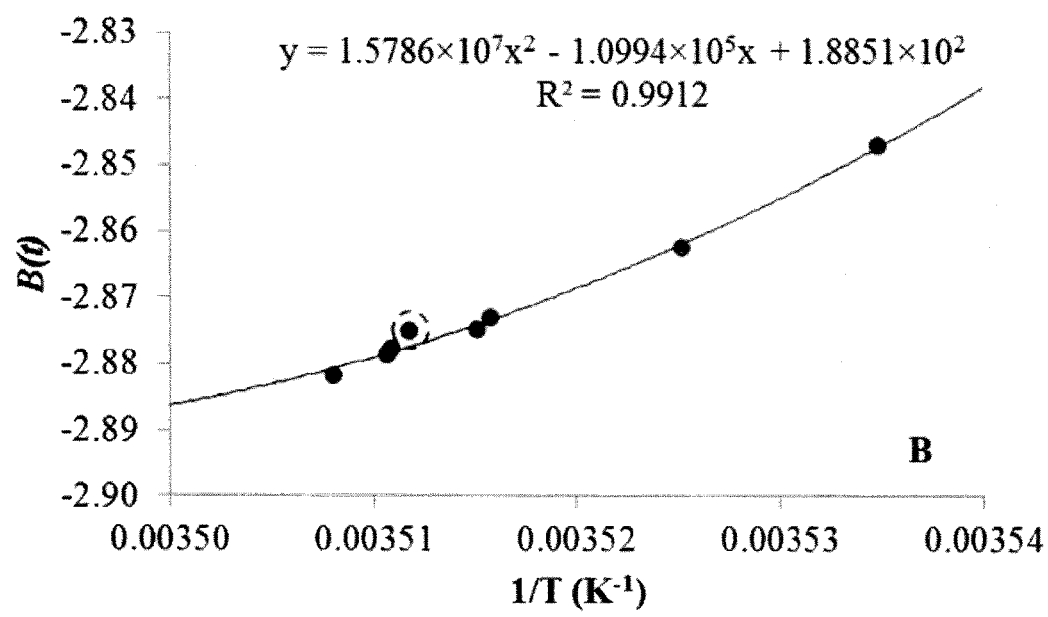

The CHANOS in situ calibration routine using CRMs allows for the determination of the B(t)-temperature function under real deployment conditions. FIG. 11B shows the B(t)-temperature curve obtained during the deployment of CHANOS in November 2013 at the WHOI Iselin dock. The in situ calibration was conducted every 48 to 72 hours. The uncertainty in B(t) relative to the best-fit line in FIG. 11B was equivalent to a DIC error of 0.1±4.9 mmol kg$^{-1}$. The larger uncertainty for the in situ calibration as compared to that obtained under laboratory conditions (FIG. 11A vs. 11B) is largely due to one data point near 1/T of 0.00351 (t=11.6° C.; circled data point in FIG. 11B). Without it, the best-fit curve has a $R^2$ value of 0.9980, equivalent to a DIC error of 1.6±2.7 mol kg$^{-1}$, comparable to that determined in the lab experiment. The cause of this apparent 'outlier' is unknown.

Given the stableness of CRM measurements during the deployment (FIG. 15) and good CRM storage in aluminum bags (FIG. 16), in situ calibration of B(t) should provide a valid means for gauging sensor consistency and performance. The coefficients of the quadratic curves between FIGS. 11A and 11B showed large differences. This might be due to the temperature dependence of the spectrophotometer and the light, which operated at different temperatures in FIGS. 11A (room temperature) and 11B (in situ temperature).

Figure 12A:
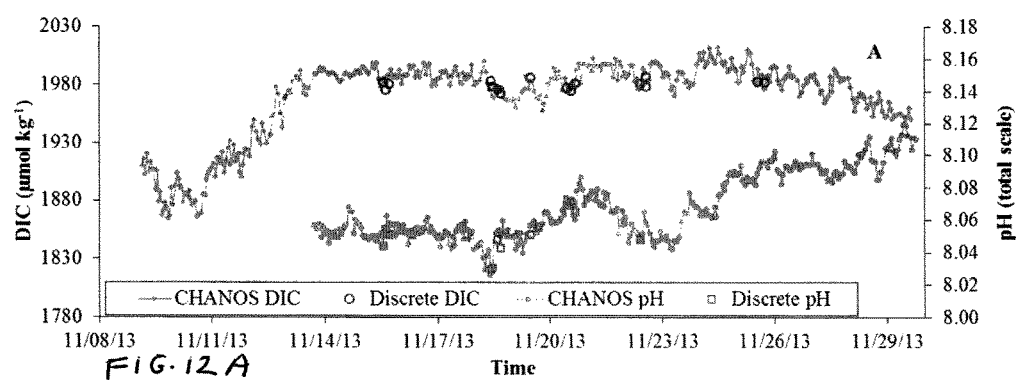
FIG. 12A is a chart of CHANOS and discrete DIC and pH measurements over time.
Figure 12B:
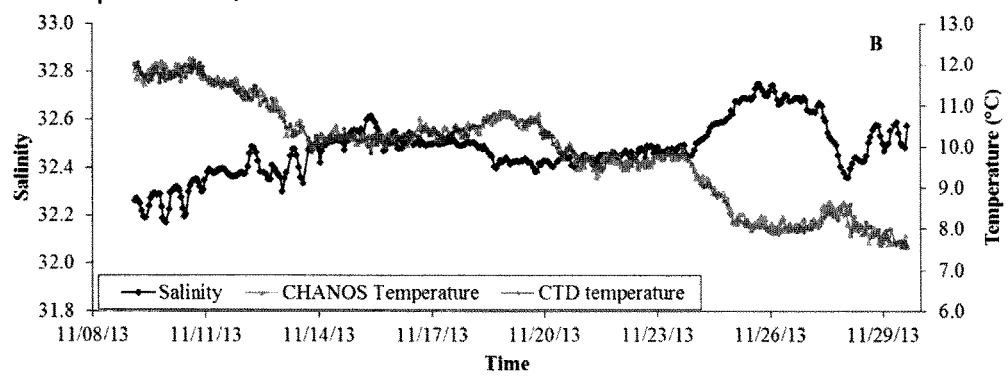
FIG. 12B is a chart of salinity and temperature during the measurement period depicted in FIG. 12A.
Figures 13A, 13B:
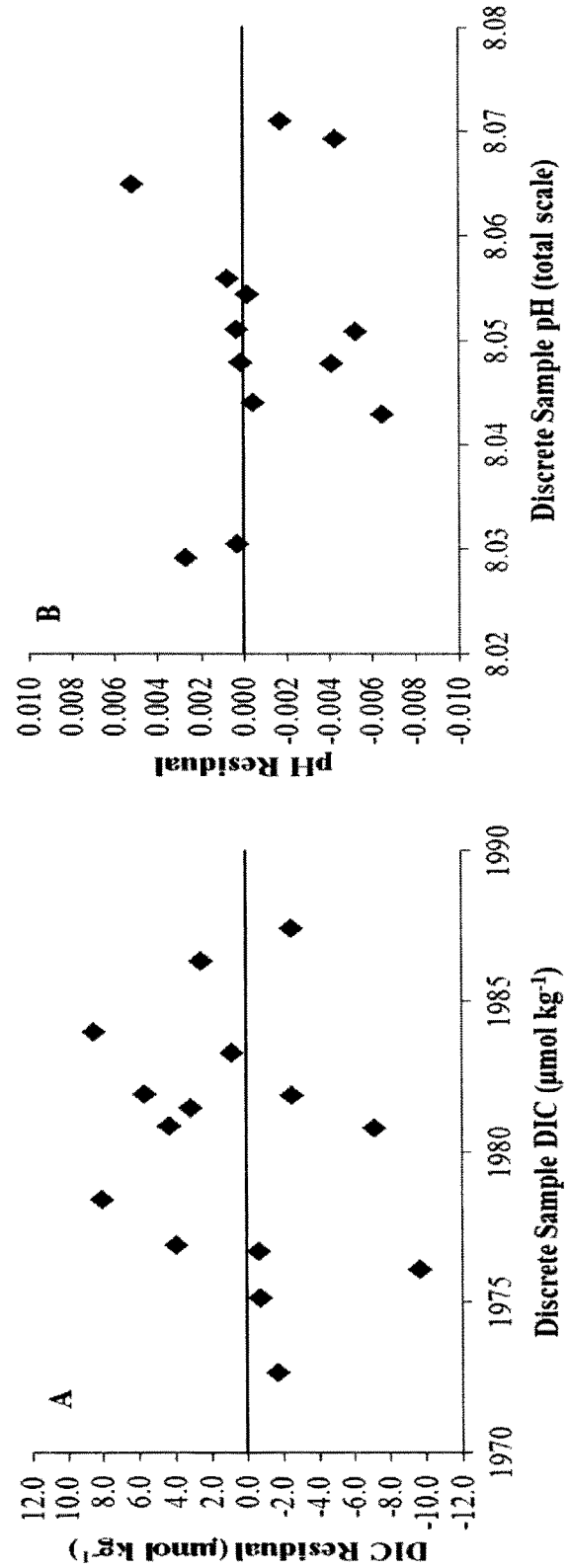
FIGS. 13A and 13B are charts of residuals between CHANOS sensor and bottle measurements over the range of sample DIC and pH, respectively, from FIGS. 12A and 12B.

During deployment at the WHOI Iselin dock, CHANOS measurements were directly compared with discrete sample measurements (FIGS. 12A-13B). The DIC channel generated more measurement data than the pH channel because the pH sample pump malfunctioned during the first week of measurement testing. During the deployment, the DIC concentration ranged from 1864 to 2012 μmol kg$^{-1}$, and pH in the total scale ($pH_T$) varied from 8.029 to 8.118 (FIGS. 12A-12B). Meanwhile, salinity only showed a small variation (32.2-32.7), and water temperature exhibited a general cooling trend of ~4.5° C. The diurnal pattern of salinity was often irregular suggesting that the hydrology may not mainly be controlled by the tide. There was a somewhat significant negative correlation between $pH_T$ and temperature ($pH_T$=-0.0147t+8.2046, $R^2$=0.7034, n=320), while DIC was not conservative relative to salinity. These observations suggest that in addition to temperature, biogeochemical processing and physical mixing may also have affected carbonate chemistry at the site.

CHANOS showed good agreement with discrete samples. The mean difference between CHANOS and discrete DIC samples was 0.8±5.2 μmol kg$^{-1}$ (n=15, FIGS. 13A-13B). The mean absolute difference was 4.1±2.9 μmol kg$^{-1}$. Part of this difference may be due to discrete sampling and analytical errors of the DIC bottle samples (~2.0 μmol kg$^{-1}$), and the rest is comparable to the precision of CHANOS (±2.5 μmol kg$^{-1}$). For pH, the mean difference between the sensor and discrete measurements was −0.0010±0.0033 pH units (n=13) with a mean absolute difference of 0.0024±0.0023 pH units (FIG. 8). Such a performance is comparable to existing in situ spectrophotometric sensors (http://www.sunburstsensors.com). Overall, CHANOS achieved the development goal, which was to make climatology-quality, simultaneous, in situ measurements of two primary $CO_2$ parameters—DIC and pH. The deployment data (FIG. 7) also indicate that the new sensor is capable of resolving the high variability of the carbonate system in dynamic environments.

For any continuous measurement, if the response is instantaneous, then continuous detection reflects the true variability of the measured parameter and has the highest spatiotemporal resolution. Otherwise (if response time >0), the measurement reflects a running average of the true variability and has reduced resolution. For shorter response times, the running average better represents the true sample variability. Currently, an estimated ~22 s response time is achieved with the continuous DIC method under partial $CO_2$ equilibration. If such a method is used on a CTD package with a lowering rate of 0.5 m s$^{-1}$ (30 m min$^{-1}$) to make continuous DIC measurements in the water column, each measurement would represent an average concentration over 11 m of water depth (0.5 m s$^{-1}$×22 s); while for the intermittent method with a response time of 5 minutes, the resolution would be 150 m (0.5 m s$^{-1}$×300 s). This represents more than one order of magnitude improvement in spatial resolution.

$CO_2$ fugacity ($fCO_2$) or partial pressure of $CO_2$ ($pCO_2$), which have similar values but slightly different physical definitions, can be measured in situ similarly as DIC. The difference is that the incoming water sample in $fCO_2$ or $pCO_2$ analysis will not be acidified as is the case in DIC analysis, so that it is dissolved $CO_2$ in the original sample that is measured. A different indicator for spectrophotometric measurements, or a different reagent for other types of sensor measurements, will be used for $fCO_2$ or $pCO_2$ measurements than that in DIC measurements.

A summary of different configurations within the scope of the present invention, for in situ uses, is provided in the following Table I:

changes in bagged CRM and changes in TA of DIC indicator solutions have occurred in the past. TA of the indicator and CRM may both change if certain layers of the multi-layered storage bags deteriorate, causing the aluminum layer to come in direct contact with the solution, or if mercury-resistant biological contamination occurs. Changes in solution DIC in bags due to $CO_2$ exchange have been observed less frequently. Improved methods for long-term storage of CRM and indicators are being studied. If the storage is robust, in situ calibration will reduce the need for laboratory calibration, which adds convenience for sensor deployment.

TABLE I

| Technique | Advantages | Disadvantages | Description |
| --- | --- | --- | --- |
| Parallel (concurrent) flow with full equilibrium | Less accurate metering pump required, fully continuous measurements, less calibration | Time lag for each recording point with slow travel through equilibration tube, but correctable. | Long flow tube for reagent, parallel flow of sample outside the reagent tube to allow full equilibrium; measurements continuously taken at end of reagent tube. |
| Parallel (concurrent) flow with partial equilibrium | Shorter tubing, less time lag | Accurate metering required for both sample and reagent; more calibration. | Shorter flow tube for reagent, parallel flow of sample outside the reagent tube to allow partial equilibrium; measurements continuously taken at the end of reagent tube. |
| Countercurrent flow with full equilibrium | Less accurate metering pump required, less calibration | Slow response time; each recording point represents a running average of a previous time interval equivalent to the response time. | Reagent in inner tube and sample in outer tube flow in opposite directions to achieve full equilibrium; measurements taken continuously but represents a running average of a previous time interval equivalent to response time. |
| Countercurrent flow with partial equilibrium | Shorter tubing, fast response time | Accurate metering required only for reagent; more calibration; each recording point. represents a running average of a previous time interval equivalent to the response time. | Reagent in inner tube and sample in outer tube flow in opposite directions to achieve partial equilibrium; measurements taken continuously but represents a running average of a previous time interval equivalent to response time. |

Note that the term "reagent" in Table I above refers to an indicator fluid, preferably a liquid, for spectrophotometric sensor measurements. Other types of sensor measurements utilize other reagents as appropriate.

For CHANOS, built-in, in situ DIC calibration has the advantage for remote deployment where discrete sampling and measurements to evaluate sensor performance is difficult. The November 2013 test data suggests that in situ calibration during the deployment is sufficient rather than taking discrete bottle samples to calibrate the system. This includes calibrating the B(t) constant with respect to temperature for all new reagents (FIG. 11B). Storage of CRM and DIC indicator are also the key to successful deployments. Although not found in this deployment, DIC and TA Alternatively, instead of using CRM, another calibrated indicator solution can be used during deployment to cross-check the stability of the primary indicator solution and to gauge measurement quality.

The modular design of CHANOS adds flexibility for future development for measurements of other parameters. Because of the similarity between spectrophotometric DIC and $pCO_2$ measurements, with minor modification, $pCO_2$ can be measured with one of the CHANOS channels using a different indicator. The main difference is that the sample will not be acidified. In alternative constructions, TA could also be measured using an improved method for single-point spectrophotometric titration. In yet other constructions, the sensor makes simultaneous measurements of any combination pair of the four primary carbonate parameters in order to meet a wide range of deployment goals.

A comparison of major characteristics of three DIC in situ sensors is provided in Table II:

TABLE II

|  | Robotic Analyzer for the TCO$_2$ System (RATS) [25] | Spectrophotometric Elemental Analysis System DIC (SEAS-DIC) [24] | Channelized Optical System (CHANOS) |
|---|---|---|---|
| Parameters measured with a single system | DIC and pH | DIC | DIC and pH |
| Principle | Conductometric DIC; Spectrophotometric pH | Spectrophotometric | Spectrophotometric |
| CO$_2$ equilibration mechanism for DIC | Static equilibration across silicone rubber | Static equilibration across Teflon AF 2400 tubing | Flow-through equilibration across Teflon AF 2400 tubing |
| Full equilibration time (for a new reagent) | <60 min | ~5 min | ~70 s for DIC; no equilibration for pH |
| Measurement frequency | Hourly | Preparation and initial CO$_2$ equilibration (~9 min in total), one recording per minute afterwards for 50 min; repeat | Preparation (~6 min for DIC and 2 min for pH), continuous flow-through measurements with an interval of every ~12 s for ~6 min for DIC and ~8 min for pH (or longer if larger-volume syringes are used); repeat (or enter a waiting mode before repeat)*. |
| Precision | ±2.7 µmol kg$^{-1}$; pH not reported | ±2 µmol kg$^{-1}$ | DIC ±2.5 µmol kg$^{-1}$ pH ±0.0010 |
| Accuracy (in situ) | ±3.6 µmol kg$^{-1}$; pH not reported | ±2 µmol kg$^{-1}$ | DIC ±4.1 µmol kg$^{-1}$ pH ±0.0024 |
| Reported deployment time | 8 weeks | ~8 days | 3 weeks |
| Measurement quality control | Lab and in situ calibration with CRM | Lab calibration with CRM | Lab and in situ calibration with CRM |
| Anti-fouling | Not reported | Copper screening; painting | Copper mesh filtering; external coverage; auxiliary pumping |
| Deployment | Stationary; Submerged to at least 1,000 m | Stationary; Submerged to maximum of 250 m | Mobile or stationary; Land, water surface, or underwater (up to 3,000 m or more) |

*Reference can be taken less frequently (e.g only once per hour) to shorten preparation steps and to capture a higher measurement frequency.

In one construction, the CO$_2$ equilibration cell (FIG. 1B) in the DIC J-box is coiled (FIG. 2B) and consists of a ~120 cm long piece of Teflon AF 2400 tubing (0.04 cm ID by 0.05 cm OD.; Random Technologies, LLC) inserted in a PEEK tubing (0.10 cm ID by 0.16 cm OD; Upchurch Scientific). A custom-made piece of PEEK tubing was used to seal the solution inside the Teflon tubing from the sample at the seawater entry and exit positions. The DIC and pH optical cells, FIGS. 2B-2C, consist of a 1 cm Z-Cell (SMA-Z-10, FIAlab Instruments, Inc) and a custom-made 10 cm PEEK rod with a 3 mm throughout borehole, respectively. The J-boxes are oil filled for pressure compensation and protection. They are connected to the other components of the sensor through tubing (for reagents and sample water), optical fibers (to light sources and spectrophotometers), and electronic cables (not shown). Two thermistors are built into each J-box to monitor sample temperature during measurements.

For the DIC channel, the components enclosed in the pressure housing include a controller board for the syringe pump stepper motors, an AD converter for reading thermistors, a power control board which sequences all of the valves and pumps during measurement operation, and a TERN 186FN microprocessor for sequencing the whole system and collecting the data. An Ocean Optics USB 4000 spectrophotometer with a serial port reads the data. Custom-made optical fibers connect the spectrophotometer to the optical Z-cell in the DIC J-box. A broadband LED source (Rebel Star, Luxeon Star LEDs) or other suitable light source is connected to the optical cell through the fibers as well. This array of equipment is duplicated to form a separate pH system, except for the pH optical cell 412, which sits outside of the J-box (FIG. 2D). The system runs on 24V DC power either through an external source or through a rechargeable battery pack. Controlling software, written in C, includes routines to read the spectrophotometer and either store the data on an internal compact flash card or transfer it to a shore computer. The system is driven by user-configured parameter sequences, which can be issued by a program on a shore server, or alternatively, can be read from a compact flash card for autonomous operation.

Four custom-made syringe pumps or other precise volumetric pumps are contained in Delrin housings and filled with pressure-balanced oil (e.g., Royal Purple #7, hydraulic oil, or other suitable oils). Each stepper motor drives a lead screw with a shaft seal, which mechanically pushes the plunger of a syringe up to 6.4 cm. Three 3 mL and one 1 mL syringes are currently used in the system. They are able to precisely deliver solution with an overall uncertainty of 2-5 µL at the rates used.

FIGS. 14A-14B summarize the operation steps of a measurement cycle for CHANOS DIC and pH channels, respectively, during the three-week field deployment. Continuous measurements within each measurement cycle (currently 6 minutes for DIC and 8 minutes for pH) can be made for a longer period of time if larger indicator and acid syringes are used. The operation steps can also be customized to achieve higher or lower resolutions of measurements to fulfill different deployment purposes. For example, the running sequence can be modified so that reference is taken less frequently and the measurement interval is longer (e.g., 2 min as compared to ~12 s), in order to save solutions and extend the measurement duration within one measurement cycle.

DIC discrete samples were measured using a DIC autoanalyzer (AS-C3, Apollo SciTech) which uses a non-dispersive infrared $CO_2$ analyzer (LiCOR 7000) for detection. This instrument has a precision and accuracy of ±2 µmol $kg^{-1}$. Discrete pH samples were measured at 25° C. based on the conventional spectrophotometric procedure using m-cresol purple on a HP 8453 spectrophotometer. Indicator perturbation and impurity were corrected. The pH measurements have a precision of ±0.0004 pH units and an accuracy of 0.001-0.002 pH units. The pH at in situ temperature was calculated by using bottle DIC and pH at 25° C. The addition of mercuric chloride to pH samples of local coastal waters did not differ from those that were not poisoned.

Figure 15:
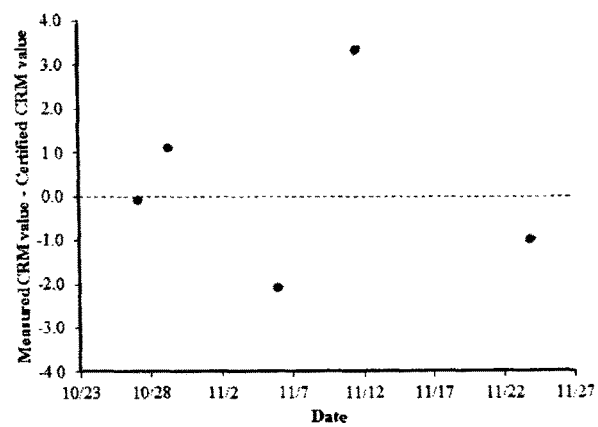
FIG. 15 is a chart comparing between measured Certified Reference Material (CRM) values by CHANOS and certified CRM values over a three-week period.

FIG. 15 shows that over the three-week period of the field deployment, the measurements of a bagged CRM (Batch #131) by the CHANOS DIC channel were within 0.3±2.1 µmol $kg^{-1}$ of the certified CRM value. These CHANOS measurements are not included in the B(t) calibration (FIG. 11B). Such results indicate that bagged CRM and indicator solution did not show detectible changes in their DIC and TA concentrations during the deployment.

Figure 16:
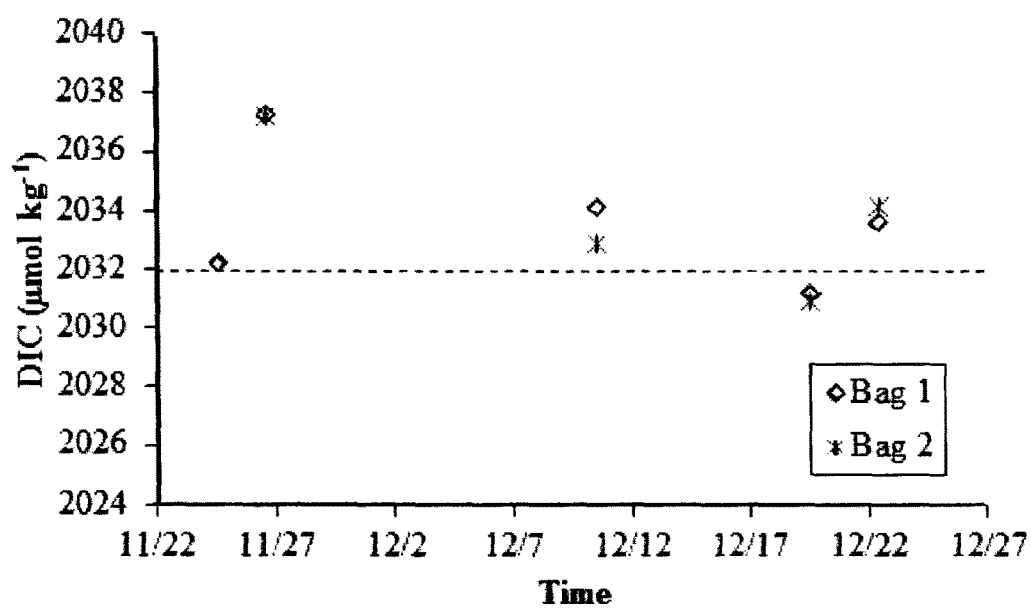
FIG. 16 is a chart comparing measurements of two laminated aluminum bags of CRM over time.

A laboratory experiment was also conducted to test the difference in DIC concentrations between two bags of CRM and to assess their stability over a four-week period (FIG. 16). Comparison between measurements of two laminated aluminum bags of CRM during the period of November 24 and Dec. 22, 2014. CRM Batch #137 (DIC=2031.9 µmol $kg^{-1}$, S=33.607) was used for the test. The dash line denotes the certified CRM value. Because of instrument issues, the data from Bag 2 on Nov. 24, 2014 is not shown. DIC samples were directly collected from the bags into glass syringes for measurements. The measurements were made using an Apollo DIC auto-analyzer (AS-C3). The mean difference in DIC concentration between the two CRM bags was 0.3±0.8 µmol $kg^{-1}$ (n=4) during the four-week period. The mean difference between the measured and the certified value was 1.7±2.3 mol $kg^{-1}$ (n=5) for Bag 1 and 1.8±2.6 mol $kg^{-1}$ (n=4) for Bag 2. These comparison metrics indicate that 1) changes in DIC when transferring the CRM to different bags should be limited through careful operation; 2) CRM stored in aluminum bags should be reasonably stable over a month-long period.

Although specific features of the present invention are shown in some drawings and not in others, this is for convenience only, as each feature may be combined with any or all of the other features in accordance with the invention. While there have been shown, described, and pointed out fundamental novel features of the invention as applied to one or more preferred embodiments thereof, it will be understood that various omissions, substitutions, and changes in the form and details of the devices illustrated, and in their operation, may be made by those skilled in the art without departing from the spirit and scope of the invention. For example, non-cylindrical passages such as baffles or other dividers can be utilized between the concurrent or countercurrent flows of the reagent and sample fluids. It is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature.

It is the intention, therefore, to be limited only as indicated by the scope of the claims appended hereto. Other embodiments will occur to those skilled in the art and are within the following claims.

What is claimed is:

1. A method for continuously measuring the concentration of at least one pre-selected dissolved gas in a sample liquid obtained from a quantity of liquid, comprising:
   selecting a sample processing cell having at least a first conduit defining a first passage with at least one gas-permeable wall configured to pass at least the preselected dissolved gas from the sample liquid into a reagent fluid, the at least one gas-permeable wall resisting flow of the sample liquid therethrough;
   continuously directing reagent fluid through the first conduit while continuously moving the sample liquid and the reagent fluid relative to each other in one of a concurrent and a countercurrent flow relationship while being separated from one another via the at least one gas-permeable wall to generate at least partially equilibrated reagent fluid;
   measuring the concentration of the dissolved gas in the at least partially equilibrated reagent fluid obtained from the first conduit utilizing a device that is separate from the sample processing cell and which enables measurement after the at least partially equilibrated reagent fluid exits from the sample processing cell; and
   wherein the reagent fluid is moved continuously through the sample processing cell and through the separate device during measuring while the sample liquid is moved continuously through the sample processing cell.

2. The method of claim 1 wherein the sample liquid is obtained continuously from the quantity of the liquid while the sample processing cell is immersed in the quantity of liquid.

3. The method of claim 1 wherein the reagent fluid includes an indicator liquid.

4. The method of claim 1 wherein measuring the concentration of the dissolved gas includes optically measuring while the at least partially equilibrated reagent fluid is in motion through the separate device.

5. The method of claim 1 wherein measuring the concentration of the dissolved gas includes spectrophotometric measurement utilizing a flow-through optical cell as the separate device.

6. The method of claim 1 wherein the sample processing cell is selected to have the at least one gas-permeable wall extending along a second conduit through which the sample liquid is conducted, and the at least one gas-permeable wall is in contact with the sample liquid in the second conduit.

7. The method of claim 1 further including measuring at least one additional parameter of the sample liquid.

8. The method of claim 1 wherein the pre-selected dissolved gas is measured over a selected period of time and is selected from at least one of dissolved inorganic carbon, carbon dioxide, and ammonia.

9. The method of claim 8 further including measuring pH of the sample liquid during the selected period of time.

10. The method of claim 1 further including periodically directing a reference fluid downstream of the sample processing cell and through the separate device to calibrate the separate device.

11. The method of claim 1 wherein the sample liquid is mixed with acid prior to entering the sample processing cell.

12. A system for continuously measuring the concentration of at least one pre-selected dissolved gas in a sample water obtained from a quantity of water, comprising:
   a sample processing cell having at least a first conduit defining a first passage with at least one gas-permeable wall configured to pass at least the pre-selected dissolved gas from the sample water into an indicator liquid, the at least one gas-permeable wall resisting flow of the sample water therethrough, the at least one gas-permeable wall extending along a second conduit through which the sample water is conducted, and the at least one gas-permeable wall being in contact with the sample water in the second conduit;
   at least one pump to direct indicator liquid continuously through the first conduit while continuously moving the sample water and the indicator liquid relative to each other in one of a concurrent and a countercurrent flow relationship while being separated from one another via the at least one gas-permeable wall to generate at least partially equilibrated indicator liquid;
   a device that is separate from the sample processing cell to measure the concentration of the dissolved gas in the at least partially equilibrated indicator liquid obtained from the first conduit, wherein the separate device enables measurement after the at least partially equilibrated indicator liquid exits from the sample processing cell; and
   a microprocessor programmed to sequence the system to perform continuous measurements according to the method of claim 1.

13. The system of claim 12 wherein the sample water is obtained continuously from the quantity of the water while the sample processing cell is immersed in the quantity of water.

14. The system of claim 12 wherein the device to measure the concentration of the dissolved gas uses spectrophotometric measurement utilizing a flow-through optical cell.

15. The system of claim 12 wherein the device measures the pre-selected dissolved gas over a selected period of time, and the pre-selected dissolved gas is selected from at least one of dissolved inorganic carbon, carbon dioxide, oxygen, and ammonia.

16. The system of claim 15 further including a device for measuring pH of the sample water during the selected period of time.

17. The system of claim 12 wherein the system is configured for installation and use in situ on at least one of an Autonomous Underwater Vehicle, a Remotely Operated Vehicle, a mobile underwater platform, and a stationary underwater platform.

18. The system of claim 12 further including a reference reservoir containing a reference liquid and connected with the separate device by a valve downstream of the sample processing cell to enable the reference liquid to be directed periodically through the separate device to calibrate the separate device.

19. The system of claim 12 wherein the sample water is mixed with acid from an acid reservoir prior to entering the sample processing cell.

20. The system of claim 12 wherein the microprocessor is programmed to sequence the system at a sampling frequency of one Hz.

21. A method for continuously measuring the concentration of at least one pre-selected dissolved gas in a sample water obtained from a quantity of water during a selected time period, comprising:
   selecting a sample processing cell having at least a first conduit defining a first passage with at least one wall for passing at least the pre-selected dissolved gas from the sample water into an indicator liquid, the at least one gas-permeable wall resisting flow of the sample water therethrough, the at least one gas-permeable wall extending along a second conduit through which the sample water is conducted, and the at least one gas-permeable wall being in contact with the sample water in the second conduit;
   continuously directing indicator liquid through the first conduit while continuously moving the sample water and the indicator liquid relative to each other in a countercurrent flow relationship while being separated from one another via the at least one gas-permeable wall to generate at least partially equilibrated indicator liquid;
   optically measuring the concentration of the dissolved gas in the at least partially equilibrated indicator liquid obtained from the first conduit utilizing a device that is separate from the sample processing cell and which enables measurement after the at least partially equilibrated indicator liquid exits from the sample processing cell; and
   wherein the indicator liquid is moved continuously through the sample processing cell and through the separate device during measuring while the sample water is moved continuously through the sample processing cell.

22. The method of claim 21 wherein the sample water is obtained at least substantially continuously from the quantity of the water and is mixed with acid prior to entering the sample processing cell.

23. The method of claim 22 wherein the pre-selected dissolved gas is measured continuously over a selected period of time and is selected from at least one of dissolved inorganic carbon, carbon dioxide, and ammonia.

24. The method of claim 23 further including measuring pH of the sample water continuously during the selected period of time.

25. The method of claim 22 wherein directing and optically measuring occurs in situ on at least one of an Autonomous Underwater Vehicle, a Remotely Operated Vehicle, a mobile underwater platform, and a stationary underwater platform.

26. The method of claim 21 further including periodically directing a reference liquid downstream of the sample processing cell and through the separate device to calibrate the separate device.

* * * * *